US006465007B1

(12) United States Patent
Eastman et al.

(10) Patent No.: US 6,465,007 B1
(45) Date of Patent: Oct. 15, 2002

(54) TRANSGENE EXPRESSION IN POLARIZED CELLS

(75) Inventors: Simon J. Eastman, Hudson; Quiming Chu, Melrose; Jennifer D. Tousignant, Cambridge; Seng H. Cheng, Wellesley; Ronald K. Scheule, Hopkinton, all of MA (US)

(73) Assignee: Genzyme Corporation, Framingham, MA (US)

( * ) Notice: Subject to any disclaimer, the term of this patent is extended or adjusted under 35 U.S.C. 154(b) by 0 days.

(21) Appl. No.: 09/340,509

(22) Filed: Jul. 1, 1999

Related U.S. Application Data

(60) Provisional application No. 60/091,608, filed on Jul. 2, 1998.

(51) Int. Cl.$^7$ .................. A61K 48/00; A61K 38/00; A61K 31/00; C12N 15/86
(52) U.S. Cl. .................. 424/450; 514/2; 514/44; 424/93.1; 424/93.2; 424/93.6; 435/455; 435/456; 435/325; 435/320.1
(58) Field of Search .................. 514/1, 44, 2; 435/455, 435/320.1, 325, 456; 424/450, 93.1, 93.2, 93.6

(56) References Cited

U.S. PATENT DOCUMENTS

| | | | | |
|---|---|---|---|---|
| 5,576,016 A | * | 11/1996 | Kim .................. | 424/450 |
| 5,635,383 A | | 6/1997 | Wu et al. ........... | 435/458 |
| 5,650,096 A | | 7/1997 | Harris et al. ........ | 252/357 |
| 5,676,954 A | | 10/1997 | Brigham et al. ..... | 424/450 |
| 5,703,055 A | | 12/1997 | Felgner et al. ....... | 514/44 |
| 5,747,471 A | | 5/1998 | Siegel et al. ........ | 514/44 |
| 5,844,107 A | * | 12/1998 | Hanson et al. ....... | 536/23.1 |
| 6,090,790 A | * | 7/2000 | Eriksson ............. | 514/44 |

FOREIGN PATENT DOCUMENTS

| | | |
|---|---|---|
| WO | WO 9104745 A | 4/1991 |
| WO | WO 9607731 | 3/1996 |
| WO | WO 9802452 A | 1/1998 |
| WO | WO 9802191 | 7/1998 |
| WO | WO 9845319 A | 10/1998 |

OTHER PUBLICATIONS

Marttin et al., J. of Drug Targeting 6: 17–36, Efficacy, safety and mechanism of cyclodextrins as absorption enhancers in nasal delivery of peptide and protein drugs, 1998.*
Freeman, D.J. and Niven, R.W., 1996, Pharmaceutical Research, 13: 202–209.*
Welsh et al., "Molecular Mechanisms of CFTR Chloride Channel Dysfunction in Cystic Fibrosis," *Cell*, 73:1251–1254 (1993).
Quinton, "Cystic Fibrosis: A disease in Electrolyte Transport", *Faseb J.*, 4:2709–2717 (1990).
Jiang et al., "Altered Fluid Transport Across Airway Epithelium in Cystic Fibrosis," *Science*, 262: 424–427 (1993).

Jiang et a., "Fluid Transport Across Cultures of Human Tracheal Glands is Altered in Cystic Fibrosis," *J. Physiol. (London)*, 501.3:637–647 (1997).
Zhang et al., "In Vivo Analysis of Fluid Transport in Cystic Fibrosis Airway Epithelial of Bronchial Xenografts," *Am. J. Physiol.*, 270:C1326–1335 (1996).
Smith et al., "Cystic Fibrosis Airway Epithelial Fail to Kill Bacteria Because of Abnormal Airway Surface Fluid," *Cell*, 85:229–236 (1996).
Adjei et al., "Bioavailability of Leuprolide Acetate Following Nasal and Inhalation Delivery to Rats and Healthy Humans," *Pharm. Res.*, 9:244–249 (1992).
Freeman & Niven, "The Influence of Sodium Glycocholate and Other Additives on the in vivo Transfection of Plasmid DNA in the Lungs," *Pharm. Res.*, 13:202–209 (1996).
Tomita et al.," Absorption–Enhancing Mechanism of EDTA, Caprate, and Decanoylcarnitine in Caco–2 Cells," *J. of Pharm. Sciences*, 85:608–611 (1996).
Tomita et al., "Absorption–Enhancing Sodium Caprate, and Decanoylcarnitine in Caco–2 Cells," *J. of Pharm. & Exp. Therap.*, 272:739–743 (1995).
Tomita et al., "Comparison of Absorption–Enhancing Effect between Sodium Caprate and Disodium Ethylenediamine-tetraacetate in Caco–2 Cells," *Biol. Pharm. Bull.*, 17(5):753–755 (1994).
Chu, Q., et al., "Binding and uptake of cationic lipid:pDNA complexes by polarized airway epithelial cells," *Hum. Gene Ther*. 10, 25–36. (1999).
Arimura et al., "Isolation and Indentification of C–type Natriuretic Peptide in Chicken Brain," *Biochem. Biphys. Res. Commun.*, 174: 142–148 (1991).
Kelly et al., "C–type Natriuretic Peptide Increases Chloride Permeability in Normal and Cystic Fibrosis Airway Cells", *Am. J. Respir. Cell Mol. Biol.*, 16:464–470 (1997).
Kelly et al., "In Vivo Activation of CFTR–Dependent Chloride Transport in Murine Airway Epithelium by CNP", *Am J. Physiol.*, 36:L1065–L1072 (1995).
Geary et al., "Role of CNP in Huyman Airways: CGMP–mediated Stimulation of Ciliary Beat Frequency", *Am. J. Physiol.*, 268:L1021–L1028 (1995).

(List continued on next page.)

*Primary Examiner*—David Guzo
(74) *Attorney, Agent, or Firm*—Finnegan, Henderson, Farabow, Garrett & Dunner L.L.P.

(57) ABSTRACT

The well-differentiated airway epithelium is the principal target tissue for gene therapy for the treatment of CF. However, recent studies have shown that gene delivery vehicles, such as cationic lipid:DNA complexes, can be inefficient at binding to and internalizing into polarized epithelial cells. The present invention provides a method to improve gene therapy by using a compound capable of disrupting tight junctions. In the practice of the invention, the transfection of a biologically active molecule by a cationic amphiphile:biologically active molecule complex or other lipid or viral or nonviral vectors is improved by treating the cells with a class of compounds known in the art as absorption enhancers or tight junction disrupting compounds.

16 Claims, 6 Drawing Sheets

OTHER PUBLICATIONS

Chrisman et al., "Seminal Plasma Factors that Cause Large Elevations in Cellular Cyclic CMP are C–type Natriuretic Peptides," *J. Bio. Chem.*, 268:3698–3703 (1993).

Abed, S.Y. et al., "Cell cycle kinetics analysis of HeLa cells exposed to aphidicolin: computer simulation," *Computers in Biology & Medicine.* 22:269–275 (1992).

Anderberg et al., "Sodium Caprate Elicits Dilatationsin Human Intestinal Tight Junctions and Enhances Drug Absorption by the Paracellular Route," *Pharmaceutical Research.* 10:857–864 (1993).

Berger, J. et al., "Secreted placental alkaline phosphatase: a powerful new quantitative indicator of gene expression in eukaryotic cells," *Gene.* 66:1–11 (1988).

Bhat, M. et al., "Regulation of tight junction permeability by calcium mediators and cell cytoskeleton in rabbit tracheal epithelium," *Pharmaceutical Research.* 10:991–997 (1993).

Caplen, N.J. et al., "Liposomemediated CFTR gene transfer to the nasal epithelium of patients with cystic fibrosis," *Nature Medicine.* 1:39–46. (1995).

Caplen, N.J. et al., "In vitro liposome–mediated DNA transfection of epithelial cell lines using the cationic liposome DC–Chol/DOPE," *Gene Therapy.* 2:603–613 (1995).

Chadwick, S.L. et al., "Safety of a single aerosol administration of escalating doses of the cationic lipid GL–67/DOPE/ DMPE–PEG5000 formulation to the lungs of normal volunteers," *Gene Therapy.* 4:937–942 (1997).

Chou, R.H. et al., "Combined effects of aphidicolin and retinoic acid on proliferation and differentiation of human leukaemic (HL–60) cells," *Cell & Tissue Kinetics.* 18:387–97 (1985).

Cornelissen, C.N. et al., "Energy–dependent changes in the gonococcal transferrin receptor," *Molecular Microbiology.* 26:25–35 (1997).

Denker, B.M. et al., "Molecular structure and assembly of the tight junction," *American Journal of Physiology.* 43:F1–F9 (1998).

Du, J. et al., "Abnormal polarization of EGF receptors and autocrine stimulation of cyst epithelial growth in human ADPKD," *American Journal of Physiology.* 269:C487–C495 (1995).

Fasbender, A. et al., "A Low Rate of Cell Proliferation and Reduced Dna Uptake Limit Cationic Lipid–mediated Gene Transfer to Primary Cultures of Ciliated Human Airway Epithelia," *Gene Therapy.* 4:1173–1180 (1997).

Fasbender et al., "Optimization of Cationic Lipidmediated Gene Transfer to Airway Epithelia," *American Journal of Physiology.* 269:L45–L51 (1995).

Felgner, et al., "Lipofection: a Highly Efficient, Lipid–mediated Dna–transfection Procedure," *Proceedings of the National Academy of Sciences of the United States of America.* 84:7413–7417 (1987).

Gill, et al., "A Placebo–controlled Study of Liposome–mediated Gene Transfer to the Nasal Epithelium of Patients with Cystic Fibrosis," *Gene Therapy.* 4:199–209 (1997).

Goldin, et al., "The Role of Cell Proliferation and Cellular Shape Change in Branching Morphogenesis of the Embryonic Mouse Lung: Analysis Using Aphidicolin and Cytochalasins," *Journal of Experimental Zoology.* 232:287–296 (1984).

Gray, et al., "Mucociliary Differentiation of Serially Passaged Normal Human Tracheobronchial Epithelial Cells," *American Journal of Respiratory Cell & Molecular Biology.* 14:104–112 (1996).

Grebenkamper, et al., "Translational Diffusion Measurements of a Fluorescent Phospholipid Between Mdck–i Cells Support the Lipid Model of the Tight Junctions," *Chemistry & Physics of Lipids.* 71:133–143 (1994).

Gumbiner, B.M., "Breaking Through the Tight Junction Barrier. *Journal of Cell Biology,*" 123:1631–1633 (1993).

Gutierrez–Merino et al., "Preferential Distribution of the Fluorescent Phospholipid Probes Nbd–phosphatidylcholine and Rhodamine–phosphatidylethanolamine in the Exofacial Leaflet of Acetylcholine Receptor–rich Membranes from Torpedo Marmorata," *Biochemistry.* 34:4846–4855 (1995).

Haldar, K. et al., "Transport of Fluorescent Phospholipid Analogues from the Erytyrocyte Membrane to the Parasite in Plasmodium Falciparum–infected Cells," *Journal of Cell Biology.* 108:2183–2192 (1989).

Holmen et al., "Efficient Lipid–mediated Transfection of Dna into Primary Rat Hepatocytes," *In Vitro Cellular & Developmental Biology. Animal.* 31:347–51 (1995).

Im et al., "Energy Dependent Insulin Binding, Internalization and Degradation in Isolated," *Journal of Molecular & Cellular Cardiology.* 18:157–168 (1986).

Keefer et al., "The alpha 2a–adrenergic Receptor Is Targeted Directly to the Basolateral Membrane Domain of Madin-–darby Canine Kidney Cells Independent of Coupling to Pertussis Toxin–sensitive Gtp–binding Proteins," Journal of Biological Chemistry. 268:11340–11347 (1993).

Lee et al., "Detailed Analysis of Structures and Formulations of Cationic Lipids for Efficient Gene Transfer to the Lung," *Hum. Gene Ther.* 7, 1701–1717 (1996).

Leventis et al., "Interactions of Mammalian Cells with Lipid Dispersions Containing Novel Metabolizable Cationic Amphiphiles," *Biochimica et Biophysica Acta.* 1023:124–132 (1990).

Matsui et al., "Loss of Binding and Entry of Liposome–dna Complexes Decreases Transfection Efficiency in Differentiated Airway Epithelial Cells," *Journal of Biological Chemistry.* 272:1117–1126 (1997).

Matter et al., "Mechanisms of Cell Polarity: Sorting and Transport in Epithelial Cells," *Current Opinion in Cell Biology.* 6:545–554 (1994).

Mcewan et al., "Polycation–induced Enhancement of Epithelial Paracellular Permeability Is Independent of Tight Junctional Characteristics," *Biochimica et Biophysica Acta.* 1148:51–60 (1993).

Moro et al., "Fluoroscence Quenching at Interfaces and the Permeation of Acrylamide and Iodide Across Phospholipid Bilayers," *Febs Letters.* 330:129–132 (1993).

Nichols et al., "Use of Fitc–labeled Influenza Virus and Flow Cytometry to Assess Binding and Internalization of Virus by Monocytesmacrophages and Lymphocytes," *Arch Virol.* 130:441–455 (1992).

Porteous et al., "Evidence for Safety and Efficacy of Dotap Cationic Liposome Mediated Cftr Gene Transfer to the Nasal Epithelium of Patients with Cystic Fibrosis," *Gene Therapy.* 4:210–218 (1997).

Rajasekaran et al., Catenins and Zonula Occludens–1 Form a Complex During Early Stages in the Assembly of Tight Junctions. *Journal of Cell Biology.* 132:451–463 (1996).

Rezai et al., "Comparison of Tight Junction Permeability for Albumin in Iris Pigment Epithelium and Retinal Pigment Epithelium in vitro," *Graefe's Arch Clin Exp Opthalmol* 253:48–55 (1997).

Remacle–bonnet et al., "Cell Polarity of the Insulin–like Growth Factor System in Human Intestinal Epithelial Cells," *Journal of Clinical Investigation.* 96:192–200 (1995).

Rose, J.k. et al., "A New Cationic Liposome Reagent Mediating Nearly Quantitative Transfection. Of Animal Cells," *Biotechniques.* 10:520–525 (1991).

Spadari et al., "Control of Cell Division by Aphidicolin Without Adverse Effects upon Resting Cells," *Arzneimittel–forschung.* 35:1108–1116 (1985).

Thatte et al., "ATP Depletion Causes Translational Immobilization of Cell Surface Transferrin Receptors in K562 Cells," *Journal of Cellular Physiology.* 166:446–452 (1996).

Tilcock, "Lipid Polymorphism," *Chemistry and Physics of Lipids.* 40:109–125 (1986).

Trivedi et al., "Liposome–mediated Gene Transfer into Normal and Dystrophin–deficient Mouse Myoblasts," *Journal of Neurochemistry.* 64:2230–2238 (1995).

Van Amersfoort et al., "Evaluation of a Flow Cytometric Fluorescence Quenching Assay of Phagocytosis of Sensitized Sheep Erythrocytes by Polymorphonuclear Leukocytes," *Cytometry.* 17:294–301 (1994).

Welsh, M.J. and Smith, A.E., "Cystic Fibrosis," *Scientific American.* 273:52–59 (1995).

Yamamoto et al., "A Mechanistic Study on Enhancement of Rectal Permeability to Insulin in the albino Rabbit," *Journal of Pharmacology & Experimental Therapeutics.* 263:25–31 (1992).

Yamashita et al., "Effect of Adjuvants of Charge–Selective Permeability and Electrical Resistance of Rat Jejunal Membrane," *Journal of Pharmaceutical Sciences.* 79 (7) (1990).

Yamaya et al., "Calciumdependent Chloride Secretion Across Cultures of Human Tracheal Surface Epithelium and Glands," *American Journal of Physiology.* 265:L170–L177 (1993).

Yew et al., "Optimization of Plasmid Vectors for High–level Expression in Lung Epithelial Cells," *Hum. Gene Ther.* 8:575–584 (1997).

Zabner et al., "Comparison of Dna–lipid Complexes and Dna alone for Gene Transfer to Cystic Fibrosis Airway Epithelia in Vivo," *Journal of Clinical Investigation.* 100:1529–1537 (1997).

Zabner et al., "Cellular and Molecular Barriers to Gene Transfer by a Cationic Lipid," *Journal of Biological Chemistry.* 270:18997–19007 (1995).

Croyle, M.A. et al., "Beta Cyclodextrins Enhance Gene Delivery to the Intestine," *Proc. of the Int. Symp. Control. Ret. Bioact. Mater.*, 24:675–676 (1997).

Midoux et al., "Specific Gene Transfer Mediated by Lactosylated POLY–L–Lysine into Hepatoma Cells,"*Nucleic Acids Research*, GB, Oxford University Press, Surrey, 21, 4: 871–878 (1993).

Buschle et al., "Transloading of Tumor Antigen–derived Peptides into Antigen–presenting Cells," *Proceedings of the National Academy of Sciences USA*, 94:3256–3261 (1997).

* cited by examiner

TRANSGENE EXPRESSION IN POLARIZED CELLS

The application claims the benefit of U.S. provisional application No. 60/091,608, filed Jul. 2, 1998.

The present invention relates to the novel use of compounds that disrupt tight junctions to facilitate the intracellular delivery (and/or transfection) of biologically active molecules by lipids, cationic amphiphilic compounds, non-viral and viral vectors.

The effective introduction of foreign genes and other biologically active molecules into targeted mammalian cells is a challenge still facing those skilled in the art. Gene therapy requires successful transfection of target cells in a patient. Transfection, which is practically useful per se, may generally be defined as a process of introducing an expressible polynucleotide (for example a gene, a cDNA, or an mRNA) into a cell. Successful expression of the encoding polynucleotide thus transfected leads to production in the cells of a normal protein and is also practically useful per se. A goal, of course, is to obtain expression sufficient to lead to correction of the disease state associated with the abnormal gene.

Examples of diseases that are targets of gene therapy include: inherited disorders such as cystic fibrosis, Gaucher's disease, Fabry's disease, and muscular dystrophy. Representative of acquired target disorders are: (1) for cancers—multiple myeloma, leukemias, melanomas, ovarian carcinoma and small cell lung cancer; (2) for cardiovascular conditions—progressive heart failure, restenosis, and hemophilias; and (3) for neurological conditions—traumatic brain injury.

Cystic fibrosis, a common lethal genetic disorder, is a particular example of a disease that is a target for gene therapy. The disease is caused by the presence of one or more mutations in the gene that encodes a protein known as cystic fibrosis transmembrane conductance regulator ("CFTR"). Cystic fibrosis is characterized by chronic sputum production, recurrent infections and lung destruction (Boat, T. F., McGraw-Hill, Inc., 1989, p. 2649–2680). Though it is not precisely known how the mutation of the CFTR gene leads to the clinical manifestation (Welsh, M. J. et al. *Cell* 73:1251–1254, 1993), defective Cl secretion and increased $Na^+$ absorption (Welsh, M. J. et al., *Cell* 73:1251–1254, 1993; Quinton, P. M., *FASEB Lett.* 4:2709–2717,1990) are well documented. Furthermore, these changes in ion transport produce alterations in fluid transport across surface and gland epithelia (Jiang, C. et al., *Science* 262:424–427, 1993; Jiang, C. et al., *J. Physiol. (London)*, 501.3:637–647, 1997; Smith, J. J. et al. *J. Clin. Invest*, 91:1148–1153, 1993; and Zhang, Y. et al., *Am.J-.Physiol* 270:C1326–1335, 1996). These resultant alterations in water and salt content of airway liquid (ASL) may diminish the activity of bactericidal peptides secreted from the epithelial cells (Smith, J. J. et al., *Cell*, 85:229–236, 1996) and/or impair mucociliary clearance, thereby promoting recurrent lung infection and inflammation.

It is widely expected that gene therapy will provide a long lasting and predictable form of therapy for certain disease states such as CF, however, there is a need to develop improved methods that facilitate entry of functional genes into cells, and whose activity in this regard is sufficient to provide for in vivo delivery of genes or other such biologically active molecules.

Effective introduction of many types of biologically active molecules has been difficult and not all the methods that have been developed are able to effectuate efficient delivery of adequate amounts of the desired molecules into the targeted cells. The complex structure, behavior, and environment presented by an intact tissue that is targeted for intracellular delivery of biologically active molecules often interfere substantially with such delivery. Numerous methods and delivery vehicles including viral vectors, DNA encapsulated in liposomes, lipid delivery vehicles, and naked DNA have been employed to effectuate the delivery of DNA into the cells of mammals. To date, delivery of DNA in vitro, ex vivo, and in vivo has been demonstrated using many of the aforementioned methods.

Though viral transfection is relatively efficient, the host immune response frequently poses a major problem. Specifically, viral proteins may activate cytotoxicity T lymphocytes (CTLs) which destroy the virus-infected cells thereby terminating gene expression in the lungs of in vivo models examined. The other problem is diminished gene transfer upon repeated administration of viral vectors due to the development of antiviral neutralizing antibodies. These issues are presently being addressed by modifying both the vectors and the host immune system, however, a more efficient method of viral transfection or delivery is also desirable.

For example, the relatively low efficacy of AdV mediated gene transfer to airway epithelial cells is a major barrier for gene therapy of CF. Gene therapy with recombinant adenoviral (AdV) vectors may also lead to inflammatory and immune responses. For applications in which repeat therapy is necessary, such as CF, these responses can limit the therapeutic usefulness of the vector. In principle, the utility of vectors may be improved by increasing its therapeutic index, i.e., by either increasing its efficacy or decreasing its toxicity. For example, a strategy that would enhance the efficacy of an adenoviral approach would allow the use of fewer virus particles to achieve a given amount of transgene expression, and thereby also reduce unwanted effects such as immune responses.

Gene transfer using AdV has been proposed as a method to treat CF. Although the ability of AdV vectors to deliver the gene encoding the cystic fibrosis transmembrane conductance regulator (CFTR) gene to airway epithelial cells has been demonstrated by many laboratories, this process has been shown to be relatively inefficient. In addition, while treatment with AdV expressing CFTR has been shown to correct the chloride channel defect in human CIF airway epithelia grown in culture, the ability to correct the enhanced sodium absorption exhibited by these cells has been much less apparent. As a result of this inefficiency, relatively high doses of AdV need to be administered in vivo to observe significant correction of physiologic deficits. Due to the undesirable host immune response associated with delivering high doses of AdV, it is desirable that both the transfer efficiency and level of expression from AdV be improved to develop an effective treatment for CF.

Additionally, non-viral and non-proteinaceous vectors have been gaining attention as alternative approaches. Because compounds designed to facilitate intracellular delivery of biologically active molecules must interact with both non-polar and polar environments (in or on, for example, the plasma membrane, tissue fluids, compartments within the cell, and the biologically active molecule itself, such compounds are designed typically to contain both polar and non-polar domains. Compounds having both such domains may be termed amphiphiles, and many lipids and synthetic lipids that have been disclosed for use in facilitating such intracellular delivery (whether for in vitro or in vivo application) meet this definition. One group of amphiphilic compounds that have showed particular promise for efficient delivery of biologically active molecules are cationic amphiphiles. Cationic amphiphiles have polar groups that are capable of being positively charged at or around physiological pH, and this property is understood in the art to be important in defining how the amphiphiles interact with the many types of biologically active molecules including, for example, negatively charged polynucleotides such as DNA.

Several recently issued U.S. patents, the disclosures of which are specifically incorporated by reference herein, have described the utility of cationic amphiphiles to deliver polynucleotides to mammalian cells. (U.S. Pat. No. 5,676,954 to Brigham et al. and U.S. Pat. No. 5,703,055 to Felgner et al.)

Although the compounds mentioned in the above-identified references have been demonstrated to facilitate the entry of biologically active molecules into cells, it is believed that the uptake efficiencies provided thereby could be improved to support numerous therapeutic applications, particularly gene therapy. Additionally, it is sought to improve the activity of the above-identified compounds so that lesser quantities thereof are necessary, leading to reduced concerns about the toxicity of such compounds or of the metabolites thereof.

Another class of cationic amphiphiles with enhanced activity is described, for example, in U.S. Pat. No. 5,747,471 to Siegel et al. issued May 5, 1998, U.S. Pat. No. 5,650,096 to Harris et al. issued Jul. 22, 1997, and PCT publication WO 98/02191 published Jan. 22, 1998, the disclosures of which are specifically incorporated by reference herein. These patents also disclose formulations of cationic amphiphiles of relevance to the practice of the present invention.

Another contributing factor to the lack of efficient intracellular delivery of biologically active molecules is the inherent difficulties in binding to the apical membrane of polarized epithelial cells. Epithelial cells are one of the most common cell types found in animals. They form boundaries between different compartments within the body and line the cavities of all the major organ systems. The major function of epithelial cells is to provide protection and to regulate transport of ions, small molecules and fluid. Epithelial cells acquire and maintain a polarized organization with respect to the membrane in order to facilitate their role as a transport regulator. Subsequently, the well-differentiated airway epithelium is the principal target tissue for gene transfer for the treatment of CF.

The plasma membrane of polarized epithelial cells is divided into apical and basolateral domains. The apical surface faces the outside environment and is specific to polarized epithelial cells. The basolateral epithelial surface has many features in common with non-epithelial cells and its major function is cell-cell and cell-substrate adhesion. These two regions of the membrane are divided by tight junctions. The tight junctions are thought to prevent uncontrolled passage of molecules across the epithelium and to help maintain a barrier between the apical and basolateral regions. Subsequently, the permeability of many therapeutic drugs is limited because of access to mainly the apical membrane.

One method of improving the permeability of therapeutic drugs is to utilize a group of compounds well known in the art which disrupt tight junctions (Adjei et al., *Pharm. Res.*, 9, pp. 244–249 (1992); Freeman & Niven, *Pharm. Res.*, 13, pp. 202–209 (1996); Tomita et al., *J. of Pharm. Sciences*, 85, pp. 608–611 (1996); and Tomita et al. *J. of Pharm. & Exp. Therap.*, 261, pp. 25–31 (1992)). The mechanism of action of all tight junction disrupting compounds is not fully understood but the fundamental idea is that the passageways between cells are widened, thus enabling larger molecules to access the basolateral region or to cross the apical membrane into another region of the body. EDTA, for example, widens the paracellular routes via calcium chelation creating access to non-apical or basolateral membranes. Other tight junction disrupting compounds increase the intracellular calcium level by an interaction with the cell membrane, also widening paracellular routes. Use of tight junction disrupting compounds has been shown to greatly improve the permeability and absorption of numerous therapeutic drugs in mammals.

Compounds capable of preventing the formation of cell-cell adhesion junctions may also improve the permeability and adsorption of therapeutic drugs. For example, HAV peptides are a series of peptides containing the sequence of histidine, alanine and valine that modulate cadherin-mediated cell adhesion.

The present invention provides for a method of improving gene therapy by treating cells with a compound capable of disrupting the tight junctions of polarized epithelial cells. The tight junction disrupting compounds increase the uptake and binding to mammalian cells of compositions employed in the art to effectuate delivery of biologically active molecules, including cationic amphiphiles and other lipids and non-viral and viral vectors. The tight junction disrupting compounds also increase transfection of biologically active molecules to epithelial cells.

The invention provides for the use of tight junction disrupting compounds that are effective for both lipid and non-lipid methods of delivering biologically active molecules including non-viral and viral vectors. The invention provides for use of tight junction disrupting compounds with all lipid complexes, along with the use of tight junction disrupting compounds with non-viral and viral vectors including adenoviruses and other methods that have been employed in the art to effectuate delivery of biologically active molecules into the cells of mammals.

In a preferred embodiment, instilling EGTA may significantly enhance the expression from a subsequent administration of adenovirus. This effect of EGTA may also enhance the ability of a subsequent aerosol of adenovirus to transfect epithelial cells. Not to be limited as to theory, the enhancing effect of EGTA may result from its ability to open epithelial tight junctions. This pretreatment strategy may improve the therapeutic index of adenovirus for applications such as CF that involve transfection of airway epithelial cells.

In a further embodiment, instilling EGTA may significantly enhance the expression from a subsequent administration of a lipid composition comprising a biologically active molecule. More preferably, the lipid composition comprises a cationic lipid or cationic amphiphile. This effect of EGTA may also enhance the ability of a subsequent aerosol of a lipid composition to transfect epithelial cells. A tight junction disrupting pretreatment strategy may improve the therapeutic index of lipid composition for applications such as CF that involve transfection of airway epithelial cells.

In another aspect, the invention provides for pharmaceutical compositions of tight junction disrupting compounds and pharmaceutical compositions of lipid and non-lipid compositions with tight junction disrupting compounds. The tight junction disrupting compounds may be an active ingredient in a pharmaceutical composition that includes carriers, fillers, extenders, dispersants, creams, gels, solutions and other excipients that are common in the pharmaceutical formulatory arts.

In a preferred embodiment, the invention provides for a method of providing gene therapy by administering a composition of a compound capable of disrupting tight junctions and a pharmaceutical composition comprising other formulations that have been employed in the art to effectuate delivery of biologically active molecules into the cells of mammals. A preferred method of administration is aerosolization.

The invention also provides for pharmaceutical compositions that comprise one or more cationic amphiphiles or adenoviruses, and one or more biologically active molecules, wherein said compositions facilitate intracellular delivery and more preferably intracellular delivery in the tissues of patients of therapeutically effective amounts of the biologically active molecules. The pharmaceutical compositions of the invention may be formulated to contain one or more additional physiologically acceptable substances that stabilize the compositions for storage and/or contribute to the successful intracellular delivery of the biologically active molecules, such as tight junction disrupting compounds.

For pharmaceutical use, the cationic amphiphile(s) of the invention may be formulated with one or more additional cationic amphiphiles including those known in the art, or with neutral co-lipids such as dioleoylphosphatidylethanolamine, ("DOPE"), to facilitate delivery to cells of the biologically active molecules. Additionally, the cationic amphiphiles, and nonviral and viral vectors may be formulated with a targeting agent or a lipid to coat the composition in order to facilitate delivery of a biologically active molecule to a targeted cell or tissue.

Additional features and advantages of the invention will be set forth in the description which follows, and in part will be apparent from the description, or may be learned by the practice of the invention. The objectives and other advantages of the invention will be realized and attained by the compounds and methods particularly pointed out in the written description and claims hereof as well as the appended drawings.

Figure 1:
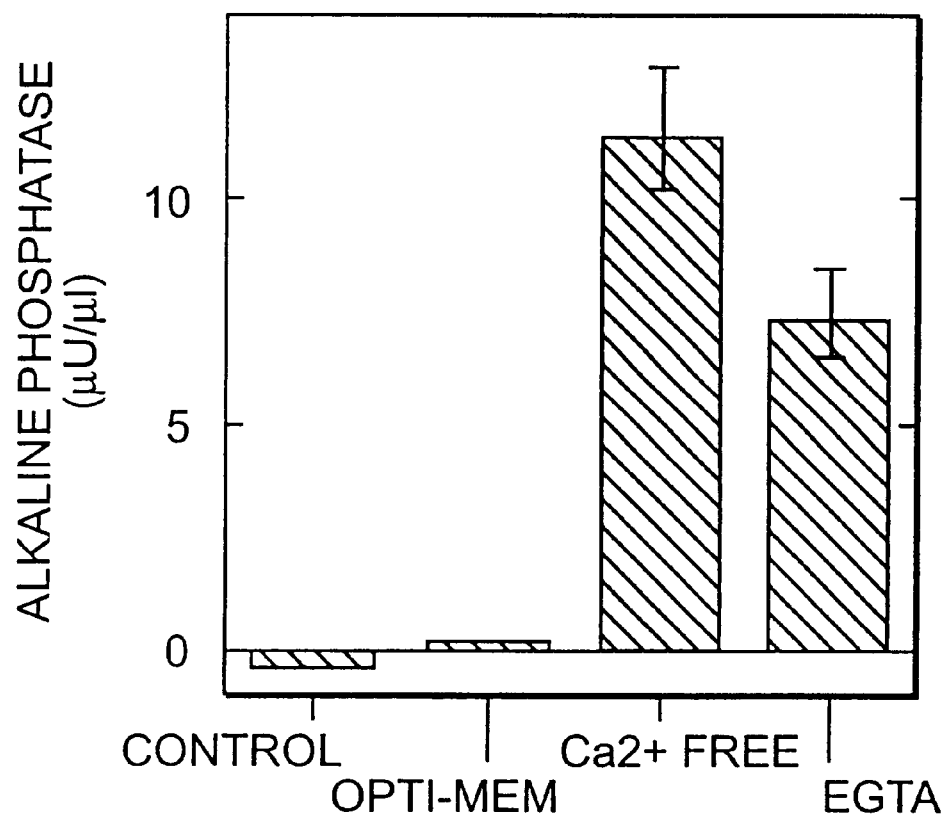
FIG. 1. Effect of $Ca^{2+}$-free medium on transgene expression by cationic lipid:pDNA complexes in polarized NHBE cells. Confluent, polarized NHBE cells on filter supports were pre-incubated at 37° C. for 0.5 h with Opti-MEM, $Ca^{2+}$-free medium, or Opti-MEM+0.1% EGTA. Cationic lipid:pDNA complexes (GL-67:pCF1-SEAP=40:53 µM) were then added and the cells incubated for 4 h at 37° C. Control cells (Control) were transfected with GL-67:pCF1Pgal (40:53 µM). After 48 h, the level of secreted alkaline phosphatase in the apical supernatant was assayed. Error bars denote SEM (n=6). See Methods for additional details.

In the present invention, lipids, including cationic amphiphile compounds, nonviral and viral vectors, including adenoviruses, and other methods that have been employed in the art to effectuate delivery of biologically active molecules into the cells of mammals, are formulated with biologically active molecules and then used in combination with tight junction disrupting compounds. These elements will now be discussed.

The invention provides for the use of tight junction disrupting compounds with any of the methods that effectuate delivery of biologically active molecules into the cells of mammals. In a preferred embodiment, tight junction disrupting compounds are used with a cationic amphiphile or a viral formulation such as a viral vector or an adenovirus.

In a preferred embodiment, the invention provides for the use of any cationic amphiphile compounds, and compositions containing them, that are useful to facilitate delivery of biologically active molecules to cells. Amphiphiles that are particularly useful facilitate the transport of biologically active polynucleotides into cells, and in particular to the cells of patients for the purpose of gene therapy.

A number of preferred cationic amphiphiles according to the practice of the invention can be found in U.S. Pat. Nos. 5,747,471 & 5,650,096 and PCT publication WO 98/02191, the disclosures of which have been specifically incorporated by reference herein. In addition to cationic amphiphile compounds, these two patents disclose numerous preferred co-lipids, biologically active molecules, formulations, procedures, routes of administration, and dosages.

In connection with the practice of the present invention, cationic amphiphiles tend to have one or more positive charges in a solution that is at or near physiological pH. Representative cationic amphiphiles that are useful in the practice of the invention are:

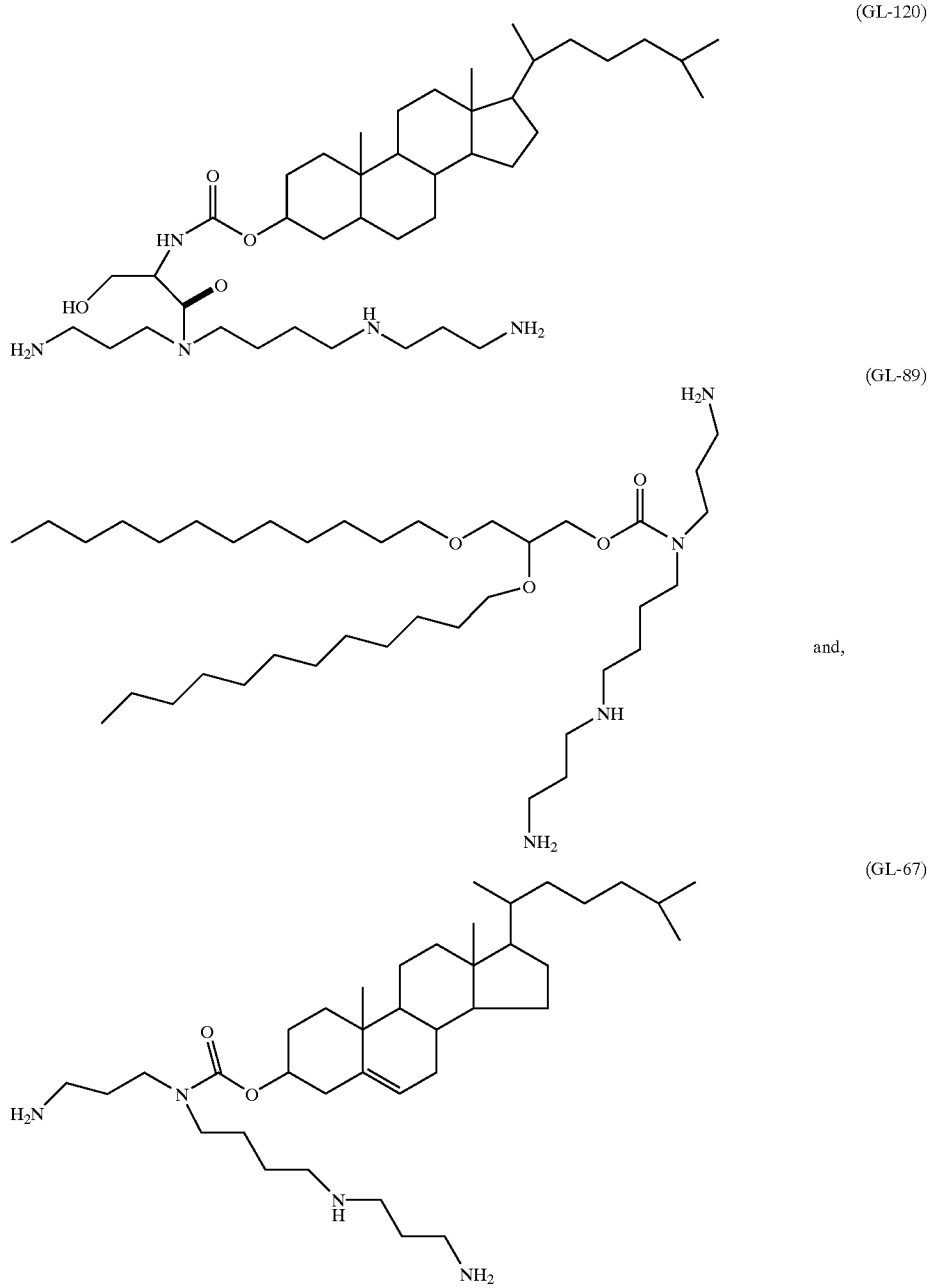

and other amphiphiles that are known in the art including those described in U.S. Pat. Nos. 5,747,471 & 5,650,096 and PCT publication WO 98/02191.

In a further preferred embodiment, the invention provides for the addition of small additional amounts of one or more derivatized polyethylene glycol compounds to a formulation comprising cationic amphiphile compounds, and compositions containing them. It has been determined that the stability of cationic amphiphile compositions may be substantially improved by adding to such formulations small additional amounts of one or more derivatized polyethylene glycol compounds. Such enhanced performance is particularly apparent when measured by stability of cationic amphiphile formulations to storage and manipulation, including in liquid (suspended) form, and when measured by stability during aerosol delivery of such formulations containing a therapeutic molecule, particularly polynucleotides.

According to the practice of the invention, any derivative of polyethylene glycol may be part of a cationic amphiphile formulation. Complexes have been prepared using a variety of PEG derivatives and all of the PEG derivatives, at a certain minimum cationic amphiphile:PEG derivative ratio have been able to form stable complexes. In a preferred embodiment, the stable complexes are homogeneous.

Not to be limited as to theory, PEG derivatives stabilize cationic amphiphile formulations and enhance the affinity of formulations to biologically active molecules. The use of PEG and PEG derivatives enables one to use a higher ratio of DNA to lipids. PEG-containing lipids were found to be effective in preventing precipitation of the complex at higher pDNA concentrations.

Only a small mole fraction of PEG-containing lipid was found to be required to form stable formulations that did not precipitate at high concentrations of lipid and DNA. For example, at 1.14 mol % DMPE-PEG$_{5000}$ (relative to the amount of total lipid), cationic lipid:pDNA complexes could be stabilized at pDNA concentrations exceeding 20 mM. Without PEG-containing lipids, a salt excipient, which is not preferred since an ionic excipient also depresses transfection activity, is required to maintain the lipid:pDNA ratio of the complex during certain methods such aerosolization. For more information regarding use of PEG derivatives the following references are specifically incorporated by reference: Simon J. Eastman et al., *Human Gene Therapy*, 8, pp. 765–773 (1997); Simon J. Eastman et al. *Human Gene Therapy*, p. 8, pp. 313–322 (1997).

Derivatives of polyethylene glycol useful in the practice of the invention include any PEG polymer derivative with a hydrophobic group attached to the PEG polymer. Examples would include PEG-PE, PEG-DMPE, PEG-DOPE, PEG-DPPE, or PEG-ceramide. Not to be limited as to theory, it is believed that preferred PEG-containing lipids would be any PEG polymer derivatives attached to a hydrophobic group that can anchor to the cell membrane. Two highly preferred species thereof include dimyristoylphosphatidylethanolamine (di C$_{14}$) ("DMPE") and dilaurylphosphatidylethanolamine (di C$_{12}$) ("DLPE").

With respect to selection of the PEG polymer, it is a preferred embodiment of the invention that the polymer be linear, having a molecular weight between 1,000 and 10,000. Preferred species thereof include those having molecular weights from 1500 to 7000, with 2000 and 5000 being examples of useful, and commercially available sizes. In the practice of the invention, it is convenient to use derivatized PEG species provided from commercial sources, and it is noted that the molecular weight assigned to PEG in such products often represents a molecular weight average, there being shorter and longer molecules in the product. Such molecular weight ranges are typically a consequence of the synthetic procedures used, and the use of any such product is within the practice of the invention.

It is also within the practice of the invention to use derivatized-PEG species that (1) include more than one attached phospholipid, or (2) include branched PEG sequence, or (3) include both of modifications (1) and (2).

Accordingly, preferred species of derivatized PEG include:

(a) polyethylene glycol 5000-dimyristoylphosphatidylethanolamine, also referred to as PEG$_{(5000)}$-DMPE;

(b) polyethylene glycol 2000-dimyristoylphosphatidylethanolamine, also referred to as PEG$_{(2000)}$-DMPE);

(c) polyethylene glycol 5000-dilaurylphosphatidylethanolamine, also referred to as PEG$_{(5000)}$-DLPE); and (d) polyethylene glycol 2000-dilaurylphosphatidylethanolamine, also referred to as PEG$_{(2000)}$-DLPE).

Certain phospholipid derivatives of PEG may be obtained from commercial suppliers. For example, the following species: di C14:0, di C16:0, di C18:0, di C18:1, and 16:0/18:1 are available as average 2000 or average 5000 MW PEG derivatives from Avanti Polar Lipids, Alabaster, Ala., USA, as catalog nos. 880150, 880160, 880120, 880130, 880140, 880210, 880200, 880220, 880230, and 880240.

The addition of neutral co-lipids to a cationic amphiphile composition is also within the practice of the invention.

However, the use of neutral co-lipids is optional. Depending on the formulation, including therein neutral co-lipids may substantially enhance delivery capabilities. Representative neutral co-lipids include dioleoylphosphatidylethanolamine ("DOPE"), the species most commonly used in the art, diphytanoylphosphatidylethanolamine, lyso-phosphatidylethanolamines other phosphatidylethanolamines, phosphatidylcholines, lyso-phosphatidylcholines and cholesterol. Typically, a preferred molar ratio of cationic amphiphile to co-lipid is about 1:1. However, it is within the practice of the invention to vary this ratio, including also over a considerable range, although a ratio from 2:1 through 1:2 is usually preferable. Use of diphytanoylphosphatidylethanolamine is highly preferred according to the practice of the present invention, as is use of "DOPE".

According to the practice of the invention, preferred formulations may also be defined in relation to the mole ratio of PEG derivative, however, the preferred ratio will vary with the cationic amphiphile chosen. In preferred examples thereof, the neutral co-lipid is diphytanoylphosphatidylethanolamine, or is DOPE, and the PEG derivative is a DMPE or DLPE conjugate of PEG$_{2000}$ or PEG$_{5000}$. In a highly preferred example, the neutral co-lipid is diphytanoylphosphatidylethanolamine, and the PEG derivative is PEG$_{(2000)}$-DMPE.

In another preferred embodiment, tight junction disrupting compounds are used with any viral formulation such as a viral vector or an adenovirus, and compositions containing them, that are useful to facilitate delivery of biologically active molecules to cells. In a further preferred embodiment, AdV is used to facilitate delivery of biologically active molecules to cells. It is also within the practice of the invention to incorporate lipids including neutral co-lipids, cationic amphiphiles, and derivatives of polyethylene glycol into a formulation containing viral and non-viral vectors.

Biologically Active Molecules

Biologically active molecules that can be useful in the practice of the invention include but are not limited to, for example, genomic DNA, cDNA, mRNA, antisense RNA or DNA, polypeptides and small molecular weight drugs or hormones. In the practice of the invention, one skilled in the art can as a matter of routine experimentation determine which molecules will be effectively delivered to a mammalian cell. It is well known in the art that once delivery of a biologically active molecule by a cationic amphiphile complex (or other lipid or non-lipid carriers) to a mammalian cell is demonstrated, the choice of other molecules for delivery is routine.

Tight Junction Disrupting Compounds

The present invention provides a method to improve gene therapy by using compounds capable of disrupting tight junctions. It is also within the practice of the invention to improve gene therapy by using compounds capable or preventing the formation of cell-cell adhesion junctions. Recent studies have shown that cationic lipid:DNA complexes can be inefficient at binding to the apical membrane of polarized epithelial cells and internalizing into the cells. In contrast, the lipid:DNA complexes do bind to cells at the edge of a polarized monolayer (eg. cells at the edge of an island of cells in which the central cells are tightly associated or cells at an artificial edge prepared by scratching an intact monolayer of cells) and are capable of binding and accumulating at proliferating epithelial cells. While the practice of the invention is not to be limited as to theory, the increased levels of accumulation is probably due to better accessability to membranes other than the apical membrane, or due to a lack of complete polarization of the cells at the edge of the monolayer. For example, a cationic amphiphile-:biologically active molecule complex may not efficiently access non-apical membranes. The cationic amphiphile:biologically active molecule complexes are in all probability too large to traverse the tight channels hindering binding and internalization.

In the practice of the invention, the transfection of a biologically active molecule by a cationic amphiphile:biologically active molecule complex or other lipid or a vial composition is improved by treating the cells with a class of compounds known in the art as absorption enhancers or tight junction disrupting compounds. Addition of these compounds has been shown to enhance absorption of a variety of drugs into human and other mammalian epithelial cells both in vitro and in vivo. The different compounds available for use in the invention to disrupt tight junctions are capable of determination by those skilled in the art.

Representative tight junction disrupting compounds that are useful in the practice of the invention include Ethylene glycol bis(B-aminoethyl ether) N,N,N',N'-tetraacetic acid (EGTA), Ethylenediaminetetraacetic acid (EDTA), palmitoyl-DL-carnitine (PC), dimethyl β-cyclodextrin (DMPCD), methyl β-cyclodextrin, α-cyclodextrin, incubation in a $Ca^{2+}$ free media, sodium glycocholate, decanoylcarnitine, and sodium caprate. There are numerous other tight junction disrupting compounds known in the art that are also embodied by the present invention such as Poly-D or L-lysine and various other cationic polymers.

The cells may be treated with tight junction disrupting compounds either prior to, simultaneously with, or as part of a pharmaceutical composition. A variety of methods of administration may be used to provide accurate dosages of the tight junction disrupting compounds including aerosolization.

In an additional embodiment, the methods and compositions of the present invention are utilized to disrupt endothelial junctions. Because of the importance of epithelial cells and more specifically polarized epithelial cells throughout the human body, tight junction disrupting compounds can be used to deliver biologically active molecules to numerous targets. For example, it is within the practice of the invention to use a tight junction disrupting compound to systemically deliver a biologically active molecule to an organ or tumor, including but not limited to the brain, heart, lung, liver, or kidney. Additionally, tight junction disrupting compounds may be used to improve the gene therapy of most disease states. The disease states that may benefit include but are not limited to cystic fibrosis, cancer, treatment of blood cells and tumors.

It is also within the practice of the invention to improve transfection of a biologically active molecule by using compounds capable of preventing the formation of cell-cell adhesion junctions. For example, HAV peptides are a series of peptides containing the sequence of histidine, alanine and valine that modulate cadherin-mediated cell adhesion. Not to be limited as to theory, cadherin complexes form cell-cell adhesion to maintain tissue integrity and generate physical and permeability barriers in the body. Cadherins have been shown to regulate epithelial, endothelial, neural and tumor cell adhesion. The cell adhesion is achieved through interactions between the extracelluar domains of cadherins between cells, and cytoplasmic domains of cadherin with the catenin proteins and the actin cytoskeleton within the cell. A tri-peptide of histidine, alanine and valine (HAV) is located in the extracellular and cytoplasmic domains of cadherin(s). The HAV peptide is crucial for hemophilic interactions between cadherins, and plays an important role in the interaction with actin cytoskeleton via the catenin proteins. HAV peptides may be linear or cyclic.

In the practice of the invention, a compound capable of preventing the formation of cell-cell adhesion junctions, such as HAV peptides, may enhance the transfection of a biologically active molecule by a composition known to facilitate delivery of biologically active molecules to cells such as a cationic amphiphile:biologically active molecule complex or other lipid or viral composition. Some HAV peptides are more potent at disrupting cell-cell adhesion junctions, and some are more potent at preventing the formation of cell-cell adhesion junctions. Based on these functions, one may use the peptides alone, or combined with tight junction disrupting agents, including but not limited to EGTA, palmitoyl-L-carnitine, dimethyl β-cyclodextrin, methyl β-cyclodextrin, or α-cyclodextrin to improve delivery of a biologically active molecule to: 1) epithelial cells, for example, delivery of the CFTR gene through cell-cell permeability barriers in airway epithelial of CF lung to enhance gene uptake on the cell basolateral membrane; 2) endothelial cells, for example, delivery of genes through brain-blood barriers to tumor cells; 3) neural cells, for example, to increase migration of the composition containing the biologically active molecule; 4) tumor cells, especially solid tumors (e.g., melanomas) since many solid tumors develop internal barriers that limit the biologically active molecule delivery to inner cells or cells distant from the injection site; and 5) muscle, liver or other whole organs by local injection with a biologically active molecule composition in order to increase migration of the composition.

Preparation of Pharmaceutical Compositions and Administration Thereof

The present invention provides for pharmaceutical compositions that facilitate intracellular delivery of therapeutically effective amounts of biologically active molecules. A pharmaceutical compositions may comprise a tight junction disrupting compound and a composition comprising a vehicle for delivery of biologically active molecules to the cell of a mammal. The invention also provides for pharmaceutical compositions that comprise a tight junction disrupting compound as the active ingredient.

Pharmaceutical compositions of the invention facilitate entry of biologically active molecules into tissues and organs such as the gastric mucosa, heart, lung, and solid tumors. Additionally, compositions of the invention facilitate entry of biologically active molecules into cells that are maintained in vitro, such as in tissue culture.

Representative biologically active molecules that can be provided intracellularly in therapeutic amounts using the methods of the invention include: (a) polynucleotides such as genomic DNA, cDNA, and mRNA that encode for therapeutically useful proteins as are known in the art; (b) ribosomal RNA; (c) antisense polynucleotides, whether RNA or DNA, that are useful to inactivate transcription products of genes and which are useful, for example, as therapies to regulate the growth of malignant cells; (d) ribozymes; and (e) low molecular weight biologically active molecules such as hormones and antibiotics.

Lipids, cationic amphiphile species, PEG derivatives, co-lipids, and viral and non-viral vectors of the invention may be blended so that two or more species are used, in combination, to facilitate entry of biologically active molecules into target cells and/or into subcellular compartments thereof. Additionally, a targeting agent may be coupled to any combination of cationic amphiphile, PEG derivative, and co-lipid or other lipid or non-lipid formulation including viral and non-viral vectors that effectuate delivery of a biologically active molecule to a mammalian cell.

Dosages of the pharmaceutical compositions of the invention will vary, depending on factors such as half-life of the biologically-active molecule, potency of the biologically-active molecule, half-life of the delivery vehicle, any potential adverse effects of the delivery vehicle or of degradation products thereof, the route of administration, the condition of the patient, and the like. Such factors are capable of determination by those skilled in the art.

A variety of methods of administration may be used to provide highly accurate dosages of the pharmaceutical compositions of the invention. Such preparations can be administered orally, parenterally, topically, transmucosally, or by injection of a preparation into a body cavity of the patient, or by using a sustained-release formulation containing a biodegradable material, or by onsite delivery using additional micelles, gels and liposomes. Nebulizing devices, powder inhalers, and aerosolized solutions are representative of methods that may be used to administer such preparations to the respiratory tract.

Additionally, the therapeutic compositions of the invention can in general be formulated with excipients (such as the carbohydrates lactose, trehalose, sucrose, mannitol, maltose or galactose, and inorganic or organic salts) and may also be lyophilized (and then rehydrated) in the presence of such excipients prior to use. Conditions of optimized formulation for each complex of the invention are capable of determination by those skilled in the pharmaceutical art. Selection of optimum concentrations of particular excipients for particular formulations is subject to experimentation, but can be determined by those skilled in the art for each such formulation.

Accordingly, a preferred aspect of the invention involves providing a composition that comprises a biologically active molecule (for example, a polynucleotide) and one or more delivery vehicles, and one or more tight junction disrupting compounds.

For example, epithelial cells grown at an air liquid interface, as well as mouse airways, especially upper airways, are relatively refractory to transfection by cationic lipid:pDNA complexes or to infection by AdV. However, treatment of epithelial monolayers with agents that disrupt epithelial tight junctions leads to a significant enhancement of lipid-based gene delivery. Treatment of polarized normal human bronchial epithelial cells with the calcium chelator EGTA resulted in a significant enhancement in our ability to transfect these cells with cationic lipid:pDNA complexes.

Similarly, a dramatic increase (~50-fold) in expression can be realized from an AdV infection of cells also treated with the calcium chelator. Not to be limited as to theory, the inefficiency of adenoviral entry into human airway cells correlates with a lack of active uptake pathway(s) at the apical membrane of fully differentiated cells. Since the pathway(s) for AdV binding and internalization are present on the basolateral surface of the epithelial cells lining human airways, agents with the potential of opening epithelial tight junctions to expose active uptake pathway(s) at the basolateral membrane may enhance AdV mediated gene transfer to epithelial cells both in vitro and in vivo. The apparent enhanced potency of AdV resulting from this strategy may represent a significant increase in the therapeutic index of this gene delivery vector, and may increase the likelihood that it can be used for indications requiring repeat administrations.

EXAMPLES

The following Examples are representative of the practice of the invention.

Example 1

Lipid:pDNA Binding and Internalization

Lipids and PDNA

Cationic lipid GL-67 was synthesized as previously described (Lee et al., Hum. Gene Ther., 7:1701–1717, 1996). Dioleoylphosphatidylethanolamine (DOPE) was from Avanti Polar Lipids (Alabaster, Ala.). Formulations of these lipids were prepared by solubilizing them in chloroform ($CHCl_3$) and then drying them down to a thin film under a stream of nitrogen. Fluorescently labeled lipid formulations were prepared by adding tracer amounts (0.33 mol % of total lipid) of N-lissamine rhodamine B phosphatidylethanolamine (Rh-PE; Avanti Polar Lipids) to the $CHCl_3$ solution. Residual $CHCl_3$ was removed under high vacuum for 1 h. Lipid films were stored at −80° C.

The plasmid vector pCF1-SEAP was constructed as described previously (Yew et al., Hum. Gene Ther., 8:575–584, 1997). Plasmids were purified using a proprietary column chromatographic procedure (Genzyme). Plasmid concentrations and purity were determined by $A_{260/280}$ measurements. Endotoxin was measured with a Limulus Amebocyte Lysate kit (BioWhittaker, Inc., Walkersville, Md.). For all preparations used, endotoxin levels were ≦50 E.U./mg of plasmid DNA. DNA concentrations given are based on an average nucleotide molecular mass of 330.

Preparation of Cationic Lipid:pDNA Complexes

Cationic lipid vesicles were prepared by hydrating lipid films of GL-67:DOPE (1:2) in water ($dH_2O$). Cationic lipid:pDNA complexes were made by preparing the vesicles at 20× the desired final concentration in $dH_2O$ and mixing them with an equal volume of 20× concentrated pDNA in $dH_2O$. After a 10 min incubation at room temperature, the complexes were diluted 10× in Opti-MEM. Complexes were labeled using either the fluorescent probe TOTO-1 (Molecular Probes, Eugene, Oreg.) at a 1:200 molar ratio of TOTO-1: nucleotides to label the pDNA or by incorporating 0.33 mol % rhodamine-PE (Avanti Polar Lipids) to total lipid in the lipid films as a lipid marker.

Cell Culture

FRT cells were grown in F12 medium (GIBCO, Gaithersburg, Md.) with 2% FBS (JRH Biosciences, Lenexa, Kans.). These cells were plated in transwell inserts (Costar 3460; 0.4 μm pore size, Cambridge, Mass.) at a density of $2 \times 10^5$ cells/12 mm diameter insert and grown until a high trans-epithelial resistance (3000–5000 $\Omega cm^2$) developed. Trans-epithelial resistance was measured using the Millicell-ERS resistance system (Millipore, Bedford, Mass.).

ATP Depletion and Measurement

To deplete intracellular ATP, polarized FRT cells were incubated with ATP depletion medium [100 mM deoxyglucose, 30 mM sodium azide (Sigma) in DMEM medium without glucose (GIBCO)] for 1 h at 37° C. Following treatment, cells were washed 3 times with PBS followed by the addition of Opti-MEM medium containing glucose. To assess the recovery of intracellular ATP levels, cells were washed 3 times with PBS, resuspended in 9 volumes of buffer (20 mM Tris, 20 mM $MgSO_4$, pH 7.8), incubated at 100° C. for 5 min, and then microcentrifuged (Thatte et al., Journal of Cellular Physiology, 166:446–452, 1996). The supernatant was assayed for ATP (ATP bioluminescent assay kit, Sigma) with a 1450 MicroBeta Trilux luminescence counter (Wallac, Gaithersburg, Md.). Cellular protein was determined using the Coomassie protein assay (Pierce, Rockford, Ill.) employing BSA as the standard.

Complex Binding and Internalization

Cells were incubated with TOTO-1 or Rh-PE labeled complexes at 37° C. for the times noted in the figure legends. Following incubation, cells were washed 7 times with cold PBS and then fixed in 2% paraformadehyde for 20 min at 4° C. The membrane of the insert was removed and mounted using immuno-mount (Shandon, Pittsburgh, Pa.) containing 2 µg/ml DAPI (Molecular Probes). Bound and internalized complexes were observed under a fluorescence microscope (Olympus, AX-70). To observe only internalized complexes, cells were washed 2 times with cold PBS and then the fluorescence of surface bound complexes was quenched by a 10 min incubation with trypan blue (1 mg/ml; Diagnostic Systems, Inc., Gibbstown, N.J.) on ice. Cells were then washed an additional 5 times with cold PBS, fixed and mounted.

To identify internalized cationic lipid:pDNA complexes without interference from the cell surface bound complexes, a method based on fluorescence in which the fluorescence of cell surface bound complexes could be quenched without quenching the fluorescence of any internalized complexes was employed. Several compounds were tested for their suitability in this regard, including trypan blue (TB), crystal violet, methylene blue, ethidium bromide, cobalt chloride, sodium iodide, picrylsulfonic acid, and acrylamide (Nichols et al., *Arch Virol.*, 130:441–455, 1992; Moro et al., *FEBS Letters*, 330:129–132, 1993; Van Amersfoort et al., *Cytometry*, 17:294–301, 1994; Gutierrez-Merino et al., *Biochemistry*, 34:4846–4855, 1995). Trypan blue was found to be the most effective and selective quencher of the fluorescence of externally-bound complexes. FRT cells incubated with fluorescently-labeled complexes for 10 min at 37° C. exhibited TOTO-1 (green) labeled complexes bound to the cell surface; the majority of the complexes should be surface-bound and not internalized at this time point. The fluorescence of these cell surface bound complexes was completely quenched following TB addition to the cells. Trypan blue was found to be equally effective at quenching the fluorescence of rhodamine-PE labeled complexes. However, because TB produced significant background fluorescence at rhodamine wavelengths, we employed TOTO-1 labeled complexes for the majority of the studies.

Energy-dependent internalization processes can be inhibited by reducing the temperature to 4° C. or by depleting intracellular ATP. We monitored the binding of complexes to the cell surface under conditions that should inhibit internalization, viz. at 37° C. following intracellular ATP depletion, and at 4° C. Internalized complexes were examined using the TB quenching method in cells at 37° C. in the presence of ATP. Consistent with previous reports that internalization should not occur at 4° C. (Im et al., *Journal of Molecular & Cellular Cardiology*, 18:157–168, 1986; Haldark et al., *Journal of Cell Biology*, 108:2183–2192, 1989; Thatte et al., *Journal of Cellular Physiology*, 166:446–452, 1996, Cornelissen et al., *Molecular Microbiology*, 26:25–35, 1997), no internalized complexes could be observed in cells incubated with complexes for 1 h at 4° C. Some complexes could be seen bound to the surface at 4° C., however, this fluorescence was effectively quenched by TB, indicating that it was confined to the extracellular space.

Using the optimal conditions for ATP depletion described above, intracellular ATP levels in polarized FTR cells fell to about 1% of their initial value. Even after medium replacement with Opti-MEM containing glucose, ATP levels recovered over 2 h to only 6 to 15% of their initial value. No energy-dependent internalization occurred at these ATP levels. In contrast, at 37° C. in the presence of normal intracellular ATP levels, a fraction of the complexes bound to the cell surface could be internalized. At 37° C., the amount of internalized complex was found to be dependent on the intracellular ATP level. The data demonstrated that TB quenching could be used to discriminate between bound and internalized complexes.

Our use of TB to quench external fluorescence is consistent with a previous report (Van Amersfoot et al., *Cytometry*, 17:294–301, 1994) that TB does not penetrate into living cells. Indeed, living cells incubated with complex at 37° C. in the presence of normal intracellular ATP levels and observed under the light microscope showed no TB staining in cells containing TOTO-1 labeled complexes. In contrast, if these cells were first fixed before the TB quenching step, no TOTO-1 labeled complexes were observed, and all cells were stained with TB under the light microscope. The results indicate that TB can be used to quench the fluorescence of surface bound complexes without the interference with the fluorescence of internalized complexes so long as the TB quenching step is carried out on living, unfixed cells.

To summarize, the intracellular ATP levels had no discernible effect on binding of the complexes to the cell surface at 37° C., indicating that binding was an energy-independent process. However, intracellular uptake of the bound complex was an energy dependent process. Binding of complexes was also seen to be much less efficient at 4° C. than at 37° C., suggesting that lower temperatures fundamentally changed the binding properties of the lipid:pDNA complexes.

Example 2

Binding and Internalization of Cationic Lipid:DNA Complexes by NHBE Cells

Cell Culture

NHBE cells (Clonetics, San Diego, Calif.) were grown as islands of more differentiated, quiescent central cells ringed by less differentiated, proliferating cells using methods described by Gray et al. *American Journal of Respiratory Cell & Molecular Biology*, 14:104–112 (1996) and Matsui et al. *Journal of Biological Chemistry*, 272:1117–1126 (1997). Briefly, NHBE cells were plated at a density of $1 \times 10^5$ cells/12 mm diameter transwell insert coated with 3 % Type I rat tail collagen gel (Collaborative, Bedford, Mass.). The basic culture medium was a 1:1 (vol:vol) mixture of DMEM with low glucose (GIBCO) and BEBM (Clonetics). All growth factors were from BEGM SingleQuots (Clonetics), except for: (I) a reduction of the hEGF (Collaborative) concentration to 0.5 ng/ml, (ii) an increase in the retinoic acid (Sigma, St. Louis, Mo.) concentration to $5 \times 10^{-8}$ M, and (iii) a supplement of 1.5 µg/ml bovine serum albumin (BSA; Sigma). Day 5 cultures were used to study the binding and internalization of cationic lipid:pDNA complexes by NHBE cells at different stages of differentiation.

Polarized NHBE cells were cultured using a modified procedure based on the methods described by Yamaya et al., *American Journal of Physiology*, 265:L170–L177 (1993), Jiang et al., *Science*, 262:424–427 (1993) and Gray et al., *American Journal of Respiratory Cell & Molecular Biology*, 14:104–112 (1996). Briefly, first passage NHBE cells were plated at a density of $2.5 \times 10^5$ cells/cm² onto inserts (Millicell-PCF, 0.4 µm pore size, Millipore) coated with human placental collagen (Sigma). The culture medium was the same as that described above for growing NHBE cells as islands. Cultures were maintained under air-liquid interface conditions starting at day 3 following the initial seeding. Cells were considered ready for use when the transepithelial resistance was •1000 Ωcm². At this point optical microscopy demonstrated polarized cells with apical microvilli and intact tight junctions.

Cell Proliferation Assay

The proliferation of NHBE cells was assessed by measuring the amount of [methyl-$^3$H] thymidine incorporation into DNA (Fasbender et al., Gene Therapy, 4:1173–1180, 1997). [Methyl-$^3$H] thymidine (5 µCi/ml; Amersham, Arlington Heights, Ill.) was added to culture medium on the basal side of polarized NHBE cells which had been pretreated with either Opti-MEM or $Ca^{2+}$-free medium. After 4 h, both groups of cells were washed 3 times with PBS and then lysed in a buffer containing 0.2% SDS, 100 mM Tris (pH=7.0), 5 mM EDTA, 200 mM NaCl, and 0.5 mg/ml proteinase K. The lysate was incubated at 65° C. for 30 min, microcentrifuged for 5 min and the supernatant placed into a fresh tube. An equal volume of isopropanol was added to precipitate the DNA. The precipitated DNA pellet was washed twice with 70% ethanol, dried, and resuspended in a 10 mM Tris-HCl, 0.5 mM EDTA buffer, pH 8.0. The DNA concentration was determined using $A_{260/280}$ measurements. Tritium counts were measured using a Beckman LS6500 scintillation counter.

Zeta Potential Measurements

Zeta potentials were measured (5 measurements per sample) with a Malvern Zetasizer 4 (Malvern Instruments, Southborough, Mass.) in a zeta cell (AZ-104 cell, Malvern Instruments Co.). Dried lipid films of GL-67:DOPE (1:2) were hydrated in distilled water ($dH_2O$). DNA (pCF1-SEAP) was diluted to a concentration of 2 mM (by nucleotides) in $dH_2O$. 0.5 ml of cationic lipid at 2× the final desired concentration (i.e. 1.5 and 3 mM GL-67) was added to an equal volume of DNA solution (2 mM) and mixed gently to prepare cationic lipid:pDNA complexes at cationic lipid:pDNA ratios of 0.75:1 and 1.5:1 mol/mol respectively. After a ten minute incubation at room temperature, the complexes were diluted ten fold in Opti-MEM and allowed to incubate for another 5 minutes before the zeta potential was measured.

Binding and Internalization of Cationic Lipid:pDNA Complexes by NHBE Cells at Different Stages of Differentiation To determine whether binding and internalization of cationic lipid:pDNA complexes was dependent on cell differentiation, NHBE cells were grown as islands on inserts as described by Matsui et al., Journal of Biological Chemistry, 272:1117–1126 (1997) and probed using the TB method. Labeled pDNA was not seen to bind or to be internalized by any of the cells of the NHBE islands. An equivalent amount of pDNA delivered as a lipid:pDNA complex was seen to bind predominately at the edges of the islands. Consistent with this observation of where the majority of the binding occurred, most of the internalized complexes were also located in these more poorly differentiated edge cells.

Complex binding to edge cells as assessed by TOTO-1 fluorescence did not appear to be a function of the surface charge of the complex. Thus, no significant difference in binding was observed between negatively charged (Zeta potential=−10.8±3.2 mV; GL-67:pDNA=0.75:1) and positively charged (Zeta potential=27.8±2.4 mV; GL-67:pDNA= 1.5:1 pM) complexes. Binding and uptake of the complexes therefore appears to be related more to the presence or absence of active uptake mechanisms in the more versus less differentiated cells than to strict surface charge effects.

To investigate the role of cellular differentiation on complex binding and internalization in more detail, separate cultures of fully polarized NHBE cells and proliferating NHBE cells were incubated with TOTO-1 labeled complexes. Little or no binding or internalization of complexes occurred in fully polarized NHBE cells in which only the apical membranes had been exposed to complex. However, consistent with the results obtained from the proliferating cells at the periphery of the islands, there was a significant amount of complex binding and internalization that could be observed over the entire cell membrane of proliferating NHBE cells. Taken together, the data suggest that NHBE cells lose the ability to bind and internalize complexes as a consequence of becoming polarized.

Basolateral membranes of polarized NHBE cells were exposed to complexes by aspirating some cells from a confluent layer of polarized cells just prior to adding labeled cationic lipid:pDNA complexes. To decrease the possibility that the complexes could be internalized by cells proliferating in response to the creation of these artificial edges, the cell layers were incubated with TOTO-1 labeled complexes immediately after creation of the edges. These manipulations did not lead to uptake of naked pDNA. However, the internalized complexes could be found in the intact cells bordering the newly generated artificial edge. Thus, a complex could be internalized by the polarized NHBE cells if access was provided to membranes other than the apical membrane. An internalized complex in these edge cells was not the result of an artifact due to a complex gaining access to the interior of dead cells, since no cell with a compromised plasma membrane (as assessed by TB staining under the light microscope) was seen to have intracellular complexes.

To confirm further that binding and internalization of cationic lipid:pDNA complexes could occur through basolateral membranes, fully polarized NHBE cells were pretreated with $Ca^{2+}$-free or EGTA-containing media to open tight junctions (Bhat et al., Pharmaceutical Research, 10:991–997, 1993; Rajasekaran et al., Journal of Cell Biology, 132:451–463, 1996; Denker et al. American Journal of Physiology, 274:F1–F9, 1998) and thereby expose the basolateral membranes. Incubating complexes with fully polarized cells, resulted in virtually no binding or internalization. However, complex internalization could be increased dramatically by pretreating the cells with $Ca^{2+}$-free medium, or with an EGTA-containing medium. Other reagents known to open tight junctions, such as EDTA, poly-lysine, sodium caprate, decanoylcarnitine and sodium glycocholate (Adjei et al., Pharmaceutical Research, 9:244–249, 1992; Yamamoto et al., Journal of Pharmacology & Experimental Therapeutics, 263:25–31, 1992; McEwan et al., Biochimica et Biophysica Acta., 1148:51–60, 1993; Grebenkamper et al., Chemistry & Physics of Lipids, 71:133–143, 1994; Tomita et al., Journal of Pharmaceutical Sciences, 85:608–611, 1996) were also examined, but EGTA was found to be the most effective at increasing the amount of internalized complex observed, and did so with minimal toxicity.

TABLE 1

Effects of Tight Junction Disrupting Compounds on Cationic Amphiphile: DNA Complex Binding

| Very Effective | Mildly Effective |
|---|---|
| Incubation in $Ca^{2+}$ free media | Sodium glycocholate |
| EGTA | Decanoylcarnitine |
| EDTA | Sodium Caprate |

Example 3
In vitro Transfection of Polarized NHBE Cells

Prior to transfection, polarized NHBE cells on inserts were incubated in either Opti-MEM, Opti-MEM containing 0.1% EGTA, or in $Ca^{2+}$-free media (Gibco) in both sides of the insert for 30 min at 37° C. The cells were then washed 3 times with Opti-MEM, and incubated with unlabeled GL-67:pCF1-SEAP (40:53 µM) for 4 h at 37° C., after which they were washed 3 times with Opti-MEM. One ml of culture medium then was added to the outside of the insert (basal side) and 100 µl added to the inside of the insert (apical side). The supernatant from the apical side was collected on day 2 after transfection, heated at 65° C. for 1 h to denature endogenous alkaline phosphatases (Berger et al., *Gene*, 1988), and assayed in triplicate for secreted alkaline phosphatase (SEAP) activity using an alkaline phosphatase reagent (Sigma) and human placental alkaline phosphatase (Calbiochem, La Jolla, Calif.) as a standard.

To inhibit NHBE cell proliferation, aphidicolin (0.5 µg/ml; Sigma) was added to culture medium on the basal side of the polarized NHBE cells for 18 h at 37° C. The cells were then transfected as described above except that the concentrations of cationic lipid and pDNA were 80 and 107 µM, respectively. After transfection, aphidicolin was present in the culture medium until the cells were harvested. Similar concentrations of aphidicolin have been found to inhibit HeLa cell proliferation after an ~15 h treatment, and the cells also required ~15 h to recover from this proliferation block (Abed, S. Y. et al., *Computers in Biology & Medicine*, 22:269–275, 1992). Retinoic acid enhanced the inhibitory effect of aphidicolin on cell proliferation (Chou, R. H. et al., *Cell & Tissue Kinetics*, 18:387–97, 1985). 0.5 µg/ml aphidicolin (~1.5 µM) in a culture medium containing 50 nM retinoic acid (see Cell Culture in the Methods) was sufficient to inhibit proliferation of NHBE cells with minimal toxicity.

In vitro Transgene Expression

The level of secreted alkaline phosphatase (SEAP) in the media from the apical side of cells was determined in fully polarized cells that had been transfected following treatment with $Ca^{2+}$-free medium or EGTA. FIG. 1 shows that pretreatment with $Ca^{2+}$-free medium resulted in an ~85-fold increase in SEAP expression; similarly, treatment with EGTA resulted in an ~55-fold increase in expression. For both $Ca^{2+}$-containing and $Ca^{2+}$-free groups, the level of transgene expression was found to be dependent on the dose of complex up to a concentration at which the cationic lipid:pDNA complexes became toxic. These data suggest that the increased internalization of complexes induced by pretreating the cells with $Ca^{2+}$-free or EGTA-containing media may also result in increased gene expression in polarized NHBE cells.

Cell proliferation

Figure 2A:
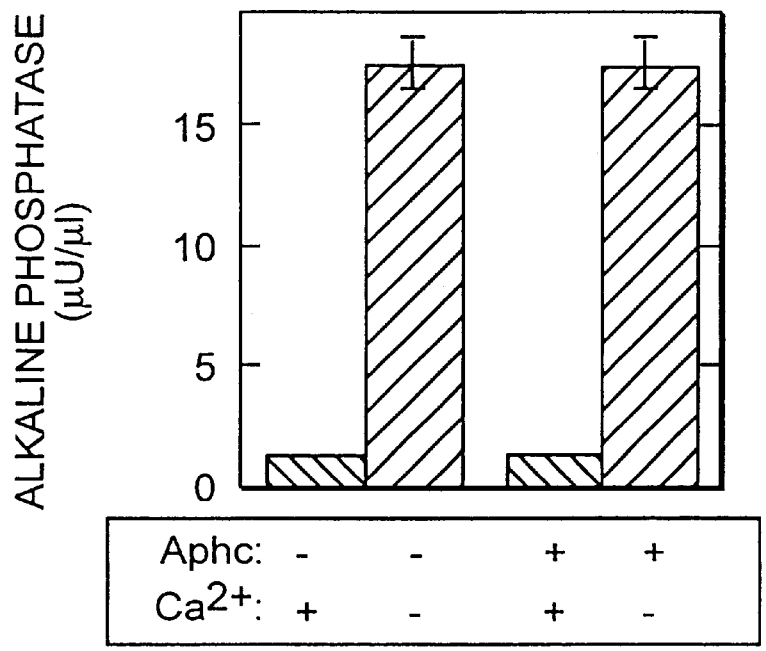
FIG. 2(A). Transgene expression by cationic lipid:pDNA complexes in fully polarized NHBE cells with aphidicolin treatment to inhibit cell proliferation. Confluent, fully polarized NHBE cells on filter supports were incubated with culture medium or culture medium containing 0.5 µg/ml aphidicolin for 18 h. Then cells were pre-treated at 37° C. for 0.5 h with Opti-MEM (open bars) or $Ca^{2+}$-free medium (filled bars), and then incubated for 4 h with GL-67:pCF1-SEAP complexes. After transfection, the medium on the basal side was replaced with culture medium with or without 0.5 µg/ml aphidicolin. The level of secreted alkaline phosphatase in the apical supernatant was assayed after 48 h. Error bars denote SEM (n=6).

To help exclude the possibility that the observed increases in transgene expression (FIG. 7) were due to cell proliferation resulting from disrupting the cellular tight junctions, the transfection efficiency of cationic lipid:pDNA complexes was measured after treating the cells with aphidicolin, which inhibits cell cycling. FIG. 2A shows that treatment with $Ca^{2+}$-free medium increased expression as already demonstrated (FIG. 1), and that aphidicolin treatment had no effect on gene expression from polarized NHBE cells, independent of whether they had been treated with $Ca^{2+}$-free medium. These results are consistent with the hypothesis that these NHBE cells are not proliferating, either before or after treating them with $Ca^{2+}$-free medium.

Figure 2B:
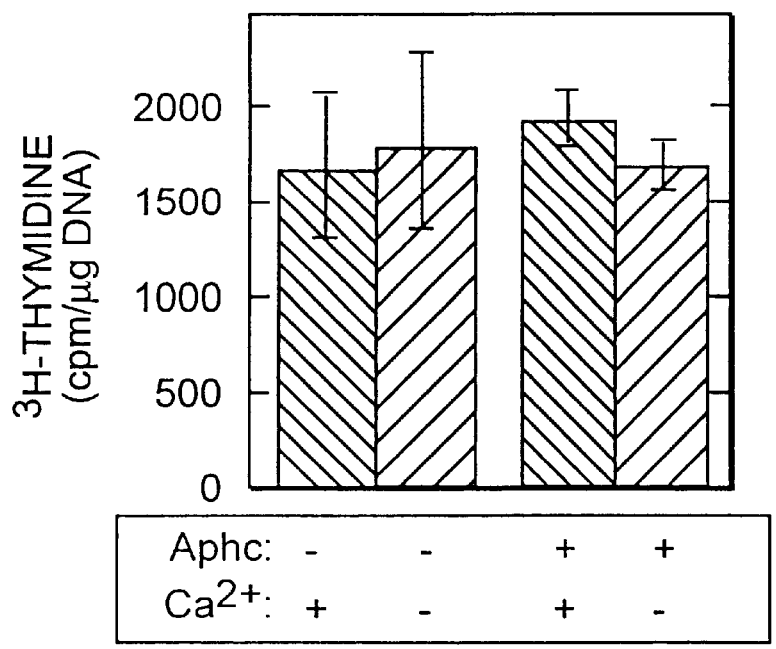
FIG. 2(B). Effects of aphidicolin and $Ca^{2+}$-free medium treatment on cell proliferation. Confluent fully polarized NHBE cells were treated as in FIG. 8A. Cells were incubated with culture medium containing [methyl-$^3$H]-thymidine for 4 h following $Ca^{2+}$-free medium. Cells were assayed for [methyl-$^3$H]-thymidine incorporation as described in the Methods. Error bars denote SEM (n=3).

To confirm further that the observed increases in transgene expression following $Ca^{2+}$-free medium treatment were not dependent on cell proliferation, the relative level of cell proliferation was quantified using [methyl-$^3$H]-thymidine incorporation into DNA (Chou, R. H. et al., *Cell & Tissue Kinetics*, 18:387–97, 1985; Fasbender, et al., *Gene Therapy*, 4:1173–1180, 1997). FIG. 2B shows that treating NHBE cells with $Ca^{2+}$-free medium in the absence of aphidicolin did not result in a significant change in [methyl-$^3$H]-thymidine incorporation, implying that the treatment with $Ca^{2+}$-free medium did not result in significant cell proliferation. FIG. 2B also shows that treating NHBE cells with $Ca^{2+}$-free medium in the presence of aphidicolin again did not result in significant change in [methyl-$^3$H]-thymidine incorporation, consistent with a quiescent state for these cells. For comparison, an identical treatment of NHBE cells grown on plastic resulted in the incorporation of 10,700±1,300 cpm/µg DNA in the absence, and 6,600±600 cpm/µg DNA in the presence of aphidicolin. Thus, the confluent and polarized NHBE cells appeared to be minimally proliferating or not proliferating, and treatment with $Ca^{2+}$-free medium for 0.5 h did not enhance their proliferation status significantly.

Example 4
Effects of Pre-treatment with $Ca^{2+}$-free Medium on Transgene Expression in Polarized NHBE Cells Cell culture NHBE cells were cultured as described previously (Chu et al., 1999). Briefly, NHBE cells were obtained (Clonetics, San Diego, Calif.), passaged once, and then plated at 2.5× $10^5$ cell S/cm$^2$ onto semi-permeable inserts (Millicell-PCF, 0.4 µm pore size, Millipore) coated with human placental collagen (Sigma, St. Louis, Mo.). The basic culture medium was a 1:1 (vol:vol) mixture of low glucose DMEM (GIBCO, Gaithersburg, Md.) and BEBM (Clonetics). All growth factors were from BEGM SingleQuots (Clonetics), except for a reduction of the hEGF (Collaborative, Bedford, Mass.) concentration to 0.5 ng/ml and an increase in the retinoic acid (Sigma) concentration to 5×10$^{-8}$ M. The cells were submerged in this culture medium for three days, and then placed under air-liquid interface conditions. NHBE cultures that developed a trans-epithelial resistance $\geq 1000$ ΩCM$^2$ were considered to be polarized and were used for infection.

Adenovirous Vectors

The Ad2βgal-4 vector was constructed as described previously (Armentano et al., 1997; Kaplan et al., 1998). Briefly, the vector is a recombinant adenovirus type 2 (Ad2) in which most of the E1 region has been replaced with an expression cassette containing the cytomegalovirus (CMV) promoter, the cDNA for nuclear-localized β-galactosidase (βgal), and an SV40 polyadenylation signal. The E3 and E4 regions are unmodified. The Ad2EGFP vector was similar except that the βgal cDNA was replaced by a cDNA encoding the enhanced green fluorescence protein (EGFP) obtained from a pEGFP plasmid (Clontech Inc., Palo Alto, Calif.), and the E4 region was replaced with open reading frame-6 (ORF-6) of E4.

Infection of Polarized NHBE Cells by Ad2βgal-4 or Ad2EGFP After Pretreatment with $Ca^{2+}$ Free Medium Polarized NHBE cells were treated with $Ca^{2+}$-free medium (GIBCO) for 0.5 h and then rinsed twice with Opti-MEM (GIBCO). As previously reported (Chu et al., 1999), this treatment resulted in the transepithelial resistance of the cells decreasing from >1000 Ω·cm$^2$ to <200 Ω·cm$^2$, the resistance of the insert membrane alone. The cells were then infected by adding 200 µl of Opti-MEM containing Ad2βgal-4 or Ad2EGFP (100 moi) to the apical surface of the cultures, while 1 ml of OptiMEM was added to the outside of the insert. After 1 h, the viral suspension was removed, the cells washed twice with Opti-MEM and then 1 ml of the culture medium was added to the outside of the insert. Two days after infection, cells were assayed for βgal expression. To monitor EGFP expression, cells were washed twice with PBS 1 day after infection and fixed in 2% paraformaldehyde in PBS (pH 7.5) for 20 min on ice. The membrane insert was excised and mounted on a slide using Immuno-mount (Shandon, Pittsburgh, Pa.) containing 2 μg/ml DAPI (Molecular Probes); EGFP expression was investigated with a fluorescence microscope (Olympus, AX-70).

Figure 3:
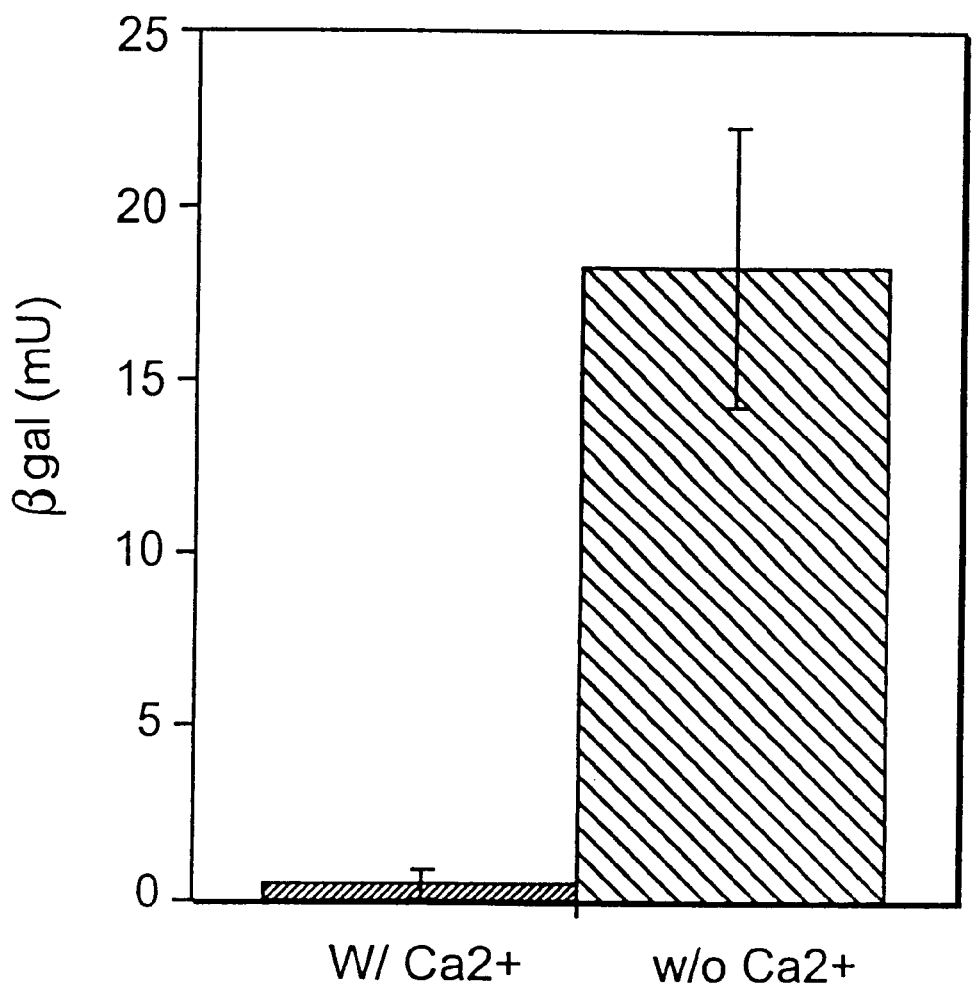
FIG. 3. Transduction of polarized NHBE cells with Ad2/βgal-4 (100 MOI) following a 0.5 h incubation with either Opti-MEM (open bar) or $Ca^{2+}$-free medium (filled bar. Expression of βgal was assayed 2 days post infection as described in Methods.

Effects of Pre-treatment with $Ca^{2+}$-free Medium on Transgene Expression in Polarized NHBE Cells To determine whether the strategy of using agents with the potential of opening epithelial tight junctions could enhance AdV mediated gene transfer in polarized NHBE cells, the effects of $Ca^{2+}$-free medium treatment on viral transduction was assessed. FIG. 3 shows that infecting polarized NHBE cells in calcium-containing medium with Ad2βgal-4 resulted in relatively low βgal expression. These results are consistent with previous reports that AdV-mediated gene transfer in polarized and differentiated epithelial cells is inefficient. However, FIG. 3 also shows that treating these same cells with Ca $^{2+}$-free medium for 0.5 h before viral infection resulted in a significant enhancement of gene expression. For example, FIG. 3 shows a 49-fold increase in β-gal expression resulting from pretreating the cells with $Ca^{2+}$-free medium before adding AdV. To rule out the possibility that EGTA might enhance the activity of AdV, the effects of EGTA on AdV titer were assessed on 293 cells. Concentrations of EGTA up to 0.4 M had no measurable effect on virus activity.

Methods to improve the efficiency of AdV mediated gene transfer to airway columnar epithelial cells are desirable for gene therapy of the CF lung. At present, a relatively high gene transfer efficiency to airway is possible if high doses of AdV are employed, e.g., (~$10^9$ IU in a mouse, unpublished data). However, host immune response are roughly proportional to the dose of AdV used. The present invention may be a more efficient method of delivering genes to polarized NHBE cells in vitro and to columnar epithelial cells in mouse trachea in vivo using relatively lower doses of AdV,(i.e. ~$10^8$ IU).

Example 5

Effects of EGTA Treatment on Gene Transfer to Mice

Instillation and Aerosolization of Ad2βgal-4 into Mice Treated with EGTA

Female BALB/c mice 9–12 weeks of age were purchased from Taconic (Germantown, N.Y.). In some groups, mice were instilled intranasally with 25 μl of a solution containing EGTA (pH 7.5), followed by 25 μl of 5% sucrose in PBS containing Adβgal-4 (2×$10^8$ IU). In other groups, mice were co-instilled with 25 μl of a solution prepared by mixing equal volumes of a 2× (4×$10^8$ IU/25 μl) Ad2βgal-4 solution in 10% sucrose with 2×EGTA prior to instillation.

Viral aerosols were generated using a MiniHEART low flow jet nebulizer (Vortran, Sacramento, Calif.). The nebulizer was operated at 50 psi with compressed medical grade air at the maximum flow rate (~2.21 pm). Animals were exposed to the aerosol in a whole-body exposure chamber. Ten ml of an Ad2βgal-4 solution (5×$10^{10}$ IU) was aerosolized over approximately one hour. Some mice were pre-treated with 50 μl of $dH_2O$ or EGTA solution by intranasal instillation 0, 15, 30, or 60 min before aerosolization, while others received no treatment prior to exposure to aerosol. X-gal staining was performed 3 days post aerosolization.

Determination of β-galactosidase Gene Expression in Mouse Lung

To quantify βgal expression, mice were sacrificed with an intraperitoneal injection of Somlethal (King Pharmaceuticals, Bristol, Tenn.) as described by Kaplan et al (1998), and samples of trachea from individual mice were homogenized in lysis buffer. βgal activity was measured with a commercial kit (Galactolight, Tropix, Bedford, Mass.). Protein concentration in the homogenate was measured using DC reagent (Bio-Rad, Hercules, Calif.). Results are expressed as relative light units (RLU) per milligram of total protein.

Cytochemical localization of Oβal expression in the trachea was observed using 5-bromo-4-chloro-3-indolyl-β-D-galactopyranoside (X-gal; Sigma). In brief, cannulated mouse lungs were fixed for 10 min by infusion of a fixing solution (2% paraformaldehyde and 0.2% glutaraldehyde in PBS). The lungs were then rinsed twice with 50 mM glycine in PBS, filled with X-gal solution, and stained overnight. Staining was stopped by transfering the samples into the fixing solution.

Light and Electron Microscopy

Tracheas stained with X-gal were removed from the fixing solution and processed for light and electron microscopy using standard procedures. Briefly, the tissues were washed with PBS, dried in alcohols, embedded in glycol methacrylate (GMA) and stained with nuclear fast red. The Oβal-stained cells were identified by light microscopy. For electron microscopy, the fixed tissues were washed three times in Sabatini's solution (1×PBS containing 6.8% sucrose), and postfixed with 1% osmium tetroxide in 0.1 M cacodylate buffer (pH7.4) for an hour, followed by three washes with Sabatini's solution. The samples were then dehydrated with a graded series of alcohols (30, 50, 75, 90 and 100 % for 15 min each), followed by treatments with propylene oxide (15 min), a 1:1 Epon-propylene oxide mix (1 h), and three incubations in pure Epon (3 h, 3 h and overnight). Polymerization was at 64° C. overnight. After embedding, ultrathin sections were cut (MT2 Sorvall ultramicrotome) and stained with lead citrate and uranyl acetate and examined with a JEOL 100CX transmission electron microscope (TEM).

Effects of EGTA Treatment on Gene Transfer to Mouse Upper Airways in vivo

Mice were instilled intranasally with Ad2CMV/βgal-4 with or without an EGTA pre-treatment. Lung cells expressing transgene were localized by X-gal staining 2–3 days after instillation. For animals instilled with Ad2CMV/βgal-4 without EGTA treatment, positively-stained cells were detected mainly in the parenchyma and small airways. There were few stained cells in the trachea or primary bronchial. These results are consistent with previous reports that mouse trachea and other upper airways are very difficult to be infected by AdV. However, if the virus was instilled 0.5 h after an EGTA treatment, gene expression was seen to be significantly enhanced in all the trachea, primary bronchi and small airways. The greatest enhancement was observed in the trachea.

To optimize the EGTA concentration required to produce this result, a semiquantitative numerical scale was established based on the relative number of βgal expressing cells. Trachea with staining levels were defined on a scale of 0 to 3, 0 indicating no cells staining for βgal, and a value of 3 indicating a large number of cells positive for the transgene. To evaluate the effect of EGTA concentration on AdV-mediated gene transfer in the trachea, mice were pre-treated with various concentrations of EGTA 0.5 h before AdV instillation. In some animals, AdV and EGTA were co-instilled. To exclude the possibility that any observed enhancement of expression was due to a hyperosmotic effect of the EGTA solution, a 20% mannitol solution (osmolarity similar to 0.4M EGTA) was included as a control in both the pre-treatment and co-instillation models.

Figure 4:
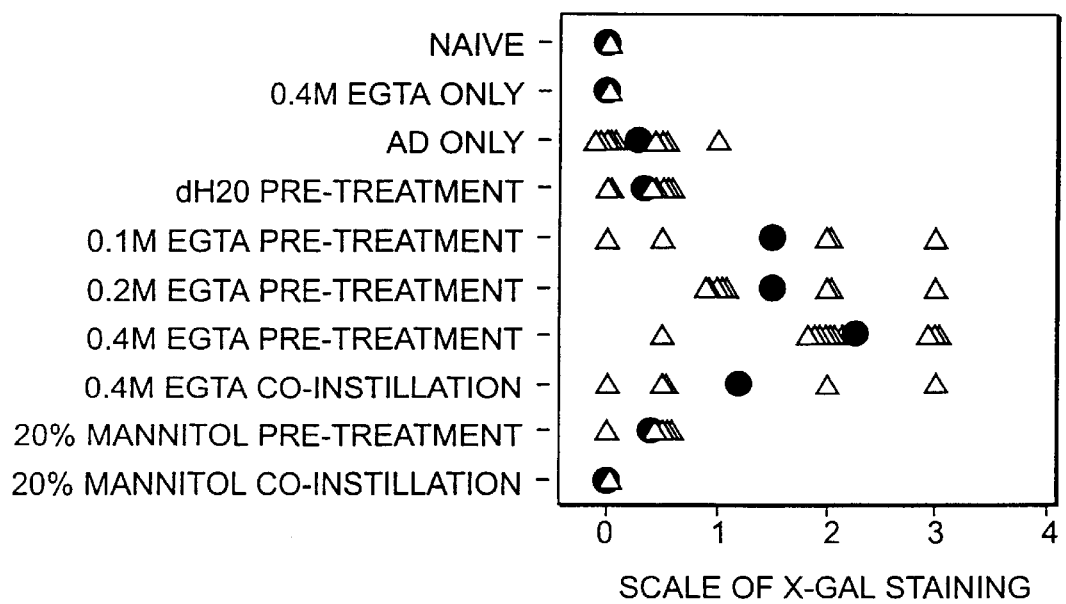
FIG. 4. Effects of EGTA concentration and osmotic agents on AdV-mediated gene expression in mouse trachea. Mice were pretreated with water, various concentrations of EGTA or mannitol and 0.5 h later instilled with $2\times10^8$ IU of. In some groups, AdV was co-instilled with EGTA or mannitol. X-gal staining was evaluated in a blinded fashion according to the scale in FIG. 12. Triangles represent individual mice; circles represent the average. (N=?)

FIG. 4 shows a marked increase in X-gal staining in the trachea of mice treated with EGTA. In contrast, X-gal staining in the groups pre-treated with $dH_2O$ or 20% mannitol was not different from that of a group given AdV alone, ie. no pretreatment. Although there was a relatively wide variation in X-gal staining among the animals of a group, the most consistent and highest X-gal staining was observed in the 0.4M EGTA pre-treatment group.

Figure 5A:
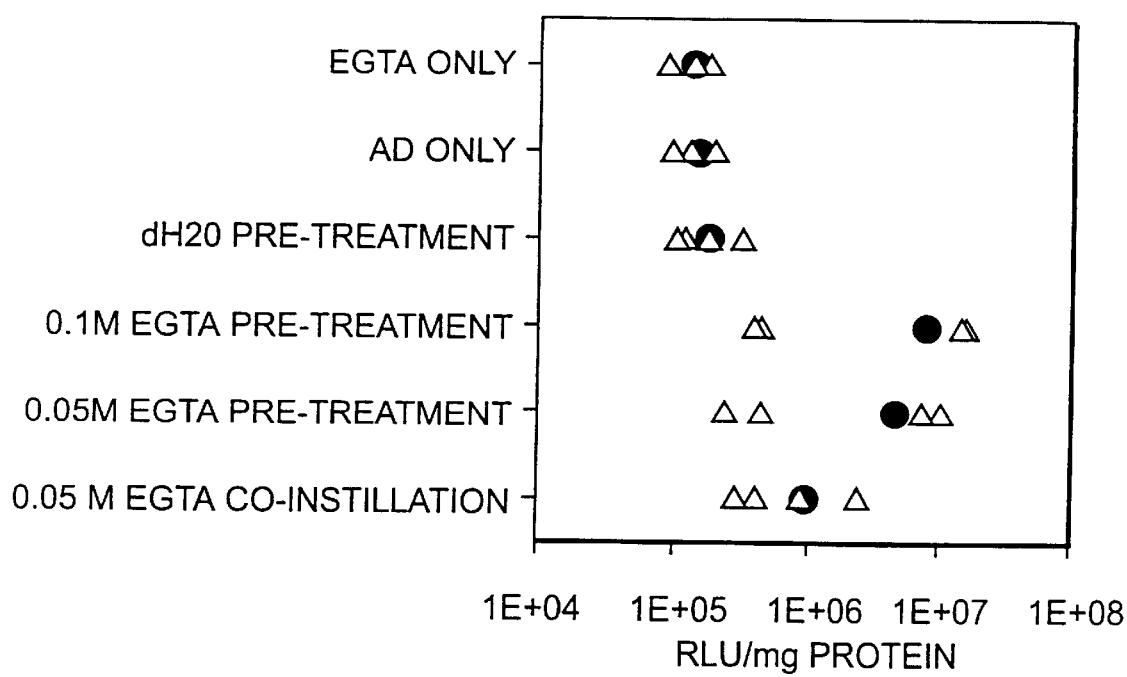
FIG. 5(A). Effect of EGTA treatment on AdV-mediated gene expression in mouse trachea quantified using a chemiluminescent assay. Mice were pre-treated with EGTA 0.5 h before instillation of $2\times10^8$ IU of $Ad_2/\beta$gal-4 in 25 µl solution. In one group, AdV was co-instilled with EGTA. Expression was evaluated after 3 days by a quantitative β-gal assay. Triangles represent RLU/mg of individual mice plotted on a log scale; circles represent the average. (N=4)

FIG. 5A shows that the same trend towards enhanced AdV-mediated transduction after EGTA treatment was seen using a quantitative chemiluminescent assay. For example, the increase in tracheal gene expression in animals pre-treated with 0.05 and 0.1M EGTA was 30- and 50-fold respectively, that of AdV alone, and >6-fold that obtained by co-instilling AdV with 0.05M EGTA. Again, this significant enhancement of gene transfer to mouse trachea was not due to hyperosmotic effect.

Figure 5B:
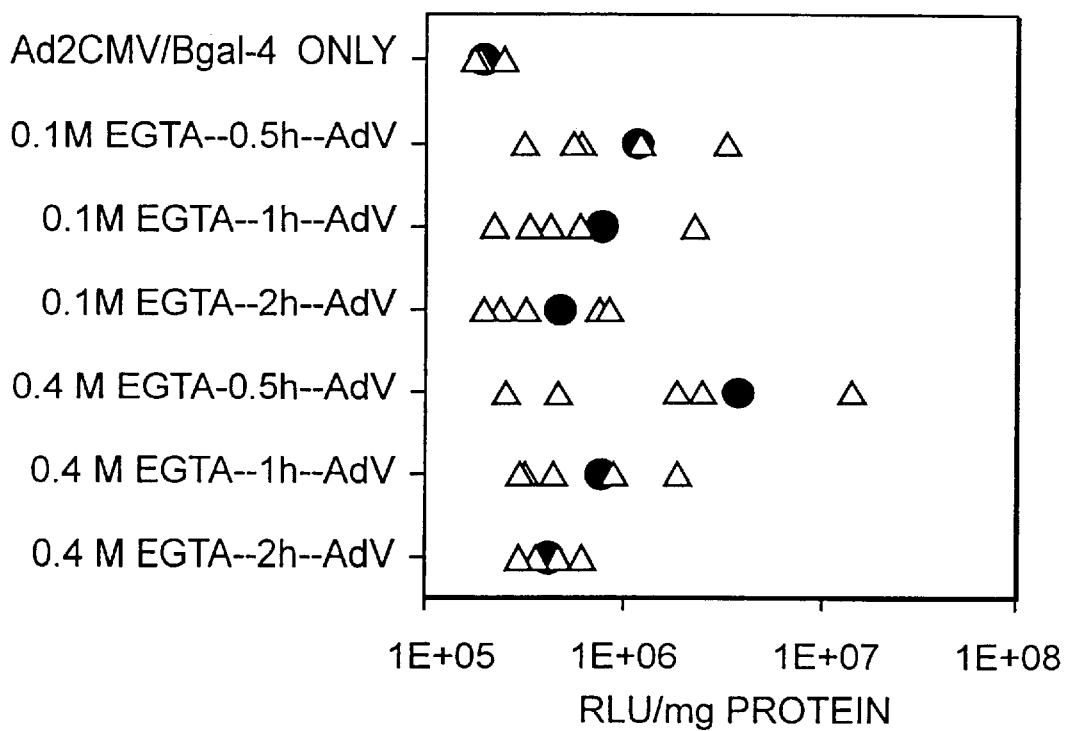
FIG. 5(B) The time-dependence effect of EGTA treatment on AdV-mediated gene transfer. Mice were pretreated with 0.1 or 0.4M EGTA and after a time delay of 0.5–2 h instilled with $2\times10^8$ IU of $Ad_2/\beta$gal-4. Expression was evaluated 3 days post infection by a quantitative P-gal assay. Triangles represent RLU/mg of individual mice plotted on a log scale; circles represent the average. (N=5)

FIG. 5B depicts the effects of varying the time interval between EGTA treatment and the instillation of virus. For two different EGTA concentrations, namely 0.1M and 0.4M, maximal enhancement of P-gal expression in mouse trachea was achieved by instilling AdV 0.5 h after the EGTA treatment. The enhancement in gene expression was gradually decreased when virus instillation occurred 1 or 2 hours after the EGTA treatment. These results demonstrate that the effects of EGTA on AdV-mediated gene transfer are time dependent. Taken together with the results in FIGS. 4 and 5A, which show a less than optimal effect of co-instilling AdV with EGTA, these results suggest that there is an optimal time window of about 0.5 hours, where the effects of EGTA provide for maximal AdV-mediated gene transfer.

Effects of EGTA on Aerosolized AdV-mediated Gene Transfer to Mouse Trachea

A likely way to deliver a gene such as CFTR into the lung epithelium is by aerosol. To find out if EGTA also would enhance gene expression by this delivery mode, aerosolized AdV was administered into mouse lung following an EGTA instillation. Very few, if any, X-gal stained cells could be observed in the trachea of mice exposed to aerosol of $Ad_2/\beta gal-4$ in absence of EGTA. However, mice that received intranasal dose of 50 µl of 0.1 M EGTA 30 min prior to expose to the aerosol demonstrated a significant number of positively stained cells. Similar increases were also observed in mice pre-treated intranasally with EGTA 0 or 15 min prior to the AdV aerosol. However, no significant increase in the number of stained cells was observed in animals pretreated 1 h prior to exposure to the AdV aerosol. A significant gene transfer to mouse trachea was also demonstrated by aerosol delivery of a lower dose ($5 \times 10^{10}$ IU/10 ml for whole body aerosol) of AdV with EGTA pretreatment. Thus, these data demonstrate that the EGTA-mediated enhancement of AdV transduction of mouse trachea is independent of the mode of delivery of the AdV.

Enhanced AdV Gene Transfer to Columnar Epithelial Cells in Mouse Trachea by EGTA Treatment The target cells for gene therapy of the CIF lung are considered to be the columnar cells that line the conducting airways. However, both mouse and human columnar cells in cartilaginous airways, i.e., trachea, are known to be particularly resistant to AdV transduction. To identify the transgene expressing cells that had been transduced by AdV, sections of mouse trachea were examined by light and electron microscopy. The instillation of AdV in the absence of EGTA led to virtually no transduction of the columnar epithelial cells of the trachea. However, β-gal expression could be found localized to columnar epithelial cells in cartilaginous airways in animals that has been treated with EGTA prior to AdV instillation. At least some of the cells transduced in these airways were ciliated cells. These results indicate that AdV can productively infect columnar epithelial cells in mouse cartilaginous airways after these airways are treated with EGTA.

In summary, the present data show that these enhancements in gene transfer seen in vitro also can be observed in vivo. The number of β-gal expressing cells was significantly increased in mouse airway, especially in the trachea, which previous studies have shown to be particularly resistant to AdV infection. Since some damaged airway epithelial cells were observed by EM in mice treated with 0.4M EGTA, the amount of B-gal expression in the trachea was quantified in mice treated with 0.1 or 0.05 M EGTA. Pre-treating with 0.1 or 0.05 M EGTA for 0.5 h resulted in at least 50 or 30-fold increases in gene expression in the trachea. The lack of β-gal expression in the tracheas of control mice treated with 0.05 to 0.4 M EGTA implies that these EGTA treatments did not upregulate the endogenous β-galactosidase.

Most of the cells transduced by AdV following an EGTA pre-treatment were identified as non-ciliated columnar epithelial. A few ciliated epithelial cells were also identified as having been transduced by AdV after EGTA treatment. Similar findings have been reported in the mouse nose using the detergent polidocanol to increase the permeability of epithelial tight junctions, i.e., enhanced AdV-mediated gene expression in non-ciliated and ciliated respiratory epithelial cells.

Not to be limited as to theory, one explanation for the ability of EGTA to enhance AdV mediated gene transfer to mouse trachea may be due to disruption of epithelial tight junctions. Consequently, this disruption might allow AdV access to active uptake pathway(s) on the basolateral membranes. Disruption of epithelial tight junctions and the time-dependent effects on epithelial tight junctions by EGTA in vitro have been well documented.

The results demonstrate a time dependent effect of EGTA on AdV-mediated gene transfer to mouse trachea in vivo (FIG. 5B). Less enhancement in gene expression was observed by instilling AdV immediately following EGTA treatment or co-instilling EGTA with AdV. The maximum increase in gene transfer was found by instilling AdV after 0.5 h after treatment with EGTA. Then the enhancements were gradually reduced by instillation of AdV after 1 or 2 h EGTA pre-treatment. However, enhancement of gene transfer may also result from osmolarity effects. For comparison, the possibilities of pre-treating with a hyperosmotic mannitol solution, or a hypoosmotic water solution were tested. No comparable enhancements in gene transfer resulted from these treatments (FIGS. 4 & 5A). Although the data are consistent with the interpretation that EGTA enhancing gene transfer by exposuring active uptake pathway(s) on basolateral membranes, other interpretations, such as enhanced AdV uptake through the apical membrane may not be rigorously excluded.

EDTA, which has a chemical structure similar to that of EGTA, has been used in a phase I clinical trial to treat CF patients with pseudomonas lung infections (Hillaman and Twigley, 1984; Brown et al., 1985; Adjei et al., 1992). In that trial, 0.2 g EDTA in 10 ml sterile water was injected via the tracheostomy into the trachea directly once per day, for 3 days; or 0.6 g EDTA in 300 ml sterile water was nebulized over 24 h via the tracheostomy into the trachea directly once per day, for 3 days. No toxic side-effects were noted. In particular, respiratory function remained unchanged, and serum calcium and magnesium levels remained normal. In another report (Brown et al., 1985), children with CF received an aerosol of 0.05M EDTA 3 times/day for 2 weeks with no adverse effects. Three out of ten could not tolerate an aerosol of 0.1 M EDTA 3 times/day for 2 weeks.

Both toxicity and efficacy factors will need to be considered to determine the viability of EGTA as a commercial treatment for CF patients. EGTA has been shown to be more effective than EDTA at disrupting tight junctions, so given equal toxicities, EGTA would be the preferred agent. However, EGTA is generally considered to be less toxic than EDTA, which may mean that higher doses of EGTA could be used than the 0.1 M EDTA that has already been used in the CF lung. In terms of efficacy, epithelial tight junctions are less tight in CF than in normal trachea and bronchial, which might argue that relatively lower concentrations of EGTA may be efficacious in CF lungs. The mouse trachea, which has tighter epithelial junctions than airways, is more difficult to infect with AdV. Epithelial tight junctions in mouse trachea may be comparable to these in human small airway, which are considered to be the target for CF gene therapy. These factors suggest that an EGTA-based treatment may eventually prove to be both safe and effective in the CF lung.

Example 6
Disruption of Epithelial Tight Junctions by EGTA Pretreatment
Lanthanum Precipitation in Trachea Under TEM Openings in tight junctions were visualized using a method described previously (Shaklai and Tavassoli, 1977; and Schneeberger and McCormack, 1984) with modifications. Briefly, mouse trachea was fixed with 2.5% glutaraldehyde, 1% lanthanum nitrate in 0.1 M cacodylate buffer, pH 7.4, for 4 to 6 h at 40 C. The trachea was then rinsed and washed 16 h with three changes of ice-cold 6.8% sucrose in 0.1 M cacodylate buffer ~pH 7.4). The samples were postfixed in 1% OsO4 in 0.1 M cacodylate buffer containing 1% lanthanum nitrate pH 7.4 at 4° C. for 1 h, and dehydrated and then embedded in epoxy resin.
Disruption of Epitheliall Tight Junctions by EGTA Pretreatment Electron microscopy was performed to determine whether the EGTA treatments used in these studies could disrupt epithelial epithelial tight junctions in mouse trachea. Consistent with previous findings, the lanthanum precipitates did not penetrate the intact epithelial tight junctions in the trachael epithelium of control animals. By contrast, in animals that had been treated with EGTA, the lanthanum precipitates penetrated through the epithelial tight junctions and came into extensive contact with the lateral membrane of these tracheal epithelial cells. These results suggest that treatment with EGTA disrupts the epithelial tight junctions of mouse trachea.

We claim:
1. A method of delivering to an epithelial cell of a mammal a composition effective for facilitating transport of a biologically active molecule into a cell, said method comprising:
   contacting said cell with a substance effective for disrupting tight junctions
   wherein said substance effective for disrupting tight junctions is chosen
      from EGTA, EDTA, poly-lysine, sodium caprate, decanoylcarnitine, palmitoyl-DL-carnitine, dimethyl β-cyclodextrin, methyl β-cyclodextrin, and
   α-cyclodextrin; and
   contacting said cell with said composition effective for facilitating transport of a biologically active molecule into a cell
   wherein the composition effective for facilitating transport of a biologically active molecule into a cell is chosen from a lipid composition and a viral composition.

2. A method of delivering to an epithelial cell of a mammal a composition effective for facilitating transport of a biologically active molecule into a cell according to claim 1, wherein said composition effective for facilitating transport of a biologically active molecule into a cell further comprises a non-viral vector.

3. A method of delivering to an epithelial cell of a mammal a composition effective for facilitating transport of a biologically active molecule into a cell according to claim 1, wherein said composition effective for facilitating transport of a biologically active molecule into a cell is a lipid composition.

4. A method of delivering to an epithelial cell of a mammal a composition effective for facilitating transport of a biologically active molecule into a cell according to claim 1, wherein said composition furthermore is effective for facilitating transfection of a biologically active molecule.

5. A method of delivering to an epithelial cell of a mammal a composition effective for facilitating transport of a biologically active molecule into a cell according to claim 1, wherein said composition furthermore is effective for binding to the said epithelial cell.

6. A method of delivering to an epithelial cell of a mammal a composition effective for facilitating transport of a biologically active molecule into a cell according to claim 3, wherein said lipid composition comprises a cationic lipid.

7. A method of delivering a biologically active molecule into a cell of a mammal comprising:
   administering an aerosolized solution to said mammal wherein said solution comprises a
      substance effective for disrupting tight junctions and
      a composition effective for facilitating transport of a biologically active molecule into a cell
   wherein said composition furthermore is effective for binding to the said cell, and wherein the composition effective for transport of a biologically active molecule into a cell is chosen from a lipid composition and a viral composition.

8. A method of delivering a biologically active molecule into a cell of a mammal according to claim 7, wherein said composition furthermore is effective for facilitating transfection of a biologically active molecule.

9. A method of delivering a biologically active molecule into a cell of a mammal according to claim 7, wherein said substance effective for disrupting tight junctions is chosen from EGTA, EDTA, poly-lysine, sodium caprate, decanoylcarnitine, sodium glycocholate, palmitoyl-DL-carnitine, dimethyl β-cyclodextrin, methyl β-cyclodextrin, and α-cyclodextrin.

10. A method of delivering a biologically active molecule into a cell of a mammal according to claim 7, wherein said composition effective for facilitating transport of a biologically active molecule into a cell further comprises a non-viral vector.

11. A method of delivering a biologically active molecule into a cell of a mammal according to claim 7, wherein said composition effective for facilitating transport of a biologically active molecule into a cell is a lipid composition.

12. A method of delivering a biologically active molecule into a cell of a mammal according to claim 11, wherein said lipid composition comprises a cationic lipid.

13. A composition comprising:
   a composition effective for facilitating transport of a biologically active molecule into a cell;
   a biologically active molecule; and
   a substance effective for disrupting tight junctions wherein said substance effective for disrupting tight junctions is chosen from EGTA, EDTA, poly-lysine, sodium caprate, decanoylcarnitine, palmitoyl-DL-carnitine, dimethyl β-cyclodextrin, methyl β-cyclodextrin, and α-cyclodextrin wherein the composition effective for facilitating transport of a biologically active molecule into a cell is chosen from a lipid composition and a viral composition, and wherein said substance effective for disrupting tight junctions is not encapsulated in said lipid composition.

14. A composition according to claim 13, wherein said composition effective for facilitating transport of a biologically active molecule into a cell further comprises a non-viral vector.

15. A composition according to claim 13, wherein said composition effective for facilitating transport of a biologically active molecule into a cell is a lipid composition.

16. A composition according to claim 15, wherein said lipid composition comprises a cationic lipid.

* * * * *